United States Patent [19]
Kamibayashi et al.

[11] 4,418,197
[45] Nov. 29, 1983

[54] 1,4-DIHYDROPYRIDINE DERIVATIVES

[75] Inventors: Masato Kamibayashi, Hasuda; Shinji Tsuchiya, Washimiya; Kozo Hiratsuka, Tsurugashima; Susumu Tsuchiya, Tanashi, all of Japan

[73] Assignee: Tokyo Tanabe Company, Limited, Japan

[21] Appl. No.: 457,867

[22] Filed: Jan. 13, 1983

[30] Foreign Application Priority Data

Feb. 1, 1982 [JP] Japan .................. 57-13398

[51] Int. Cl.³ ................ C07D 401/14; C07D 401/12
[52] U.S. Cl. .................. 546/256; 546/279; 424/266
[58] Field of Search .............. 546/256, 279

[56] References Cited

U.S. PATENT DOCUMENTS

| | | | |
|---|---|---|---|
| 3,905,970 | 9/1975 | Bossert et al. | 424/256 |
| 3,946,027 | 3/1976 | Bossert et al. | 546/256 |
| 4,146,627 | 3/1979 | Wehinger | 546/279 |
| 4,380,547 | 4/1983 | Materne | 546/279 |

FOREIGN PATENT DOCUMENTS 56-140989 11/1981 Japan .................. 546/256

*Primary Examiner*—Jane T. Fan
*Attorney, Agent, or Firm*—McGlew and Tuttle

[57] ABSTRACT

Novel 1,4-dihydropyridine derivatives of the formula [I] are provided:

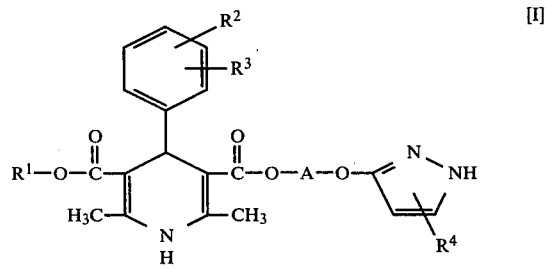

wherein $R^1$ represents a $C_{1-4}$ alkyl group or a $C_{3-6}$ alkoxyalkyl group, $R^2$ represents hydrogen or halogen, $R^3$ is either nitro when $R^2$ is hydrogen, or halogen when $R^2$ is halogen, $R^4$ represents a pyridyl group, a phenethyl group, an unsubstituted benzyl group, a substituted benzyl group having one or more suitable substituents, an unsubstituted phenyl group, or a substituted phenyl group having one or more suitable substituents, and A represents an unsubstituted hexamethylene group or a substituted hexamethylene group having one or two $C_{1-3}$ alkyl groups. The 1,4-dihydropyridine derivatives have vasodilating and hypotensive activity which is kept for a long period, and are useful in the treatment of cardiovascular disease and hypertension.

18 Claims, No Drawings

1,4-DIHYDROPYRIDINE DERIVATIVES

BACKGROUND OF THE INVENTION

The present invention relates to novel 1,4-dihydropyridine derivatives having hypotensive effect.

Heretofore, there have been known, as 1,4-dihydropyridine derivatives, 4-(2-nitrophenyl)-2,6-dimethyl-1,4-dihydropyridine-3,5-dicarboxylic acid dimethyl ester (U.S. Pat. No. 3,644,627; hereinafter referred to as Nifedipine), 4-(3-nitrophenyl)-2,6-dimethyl-1,4-dihydropyridine-3,5-dicarboxylic acid 3-methyl ester 5-$\beta$-(N-benzyl-N-methylamino)ethyl ester hydrochloride (Japanese Patent Publication No. 45075/1980; hereinafter referred to as Nicardipine) etc. which are useful as therapeutic agents for improving the coronary circulation or the cerebral circulation.

However, it has been reported based on an animal test that the vasodilating effect and the hypotensive effect resulting from said effect of these compounds disappear within a short period of time, such as 30–40 minutes or so, at the effective intravenous dosage at which they become significant, for example, 10 $\mu$g/kg, and also that these compounds have an effect to increase the heart rate which means one element to increase the burden on the function of the heart, in other words, which can also be said a kind of side effect (Arzneimittel-Forschung, Vol. 22, No. 1, p. 33, 1972; ibid., Vol. 26, No. 12, p. 2172, 1976; Toho Igakukai Zasshi, Vol. 26, No. 2, p. 48, 1972). Therefore, when these compounds are to be employed as remedies for hypertension, cardiovascular diseases etc. which require continuous use of drug for a prolonged period of time, the improvement of the preparation, for example, by making it slow-releasing etc., frequent administration, or use in combination with other drugs is needed.

SUMMARY OF THE INVENTION

The present invention relates to 1,4-dihydropyridine derivatives which possess a long-lasting hypotensive effect resulting from the vasodilating effect and are of very low ability to change the heart rate.

According to the present invention, there are provided 1,4-dihydropyridine derivatives of the following general formula [I]:

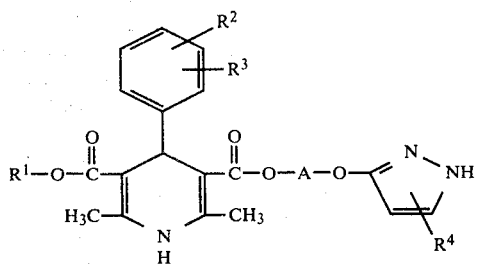

[I]

wherein $R^1$ represents an alkyl group having from 1 to 4 carbon atoms or an alkoxyalkyl group having from 3 to 6 carbon atoms, $R^2$ represents a hydrogen atom or a halogen atom, $R^3$ represents either a nitro group when $R^2$ is a hydrogen atom or a halogen atom when $R^2$ is a halogen atom, $R^4$ represents a pyridyl group, a phenethyl group, a benzyl group which may optionally be substituted by at least one member selected from the group consisting of a lower alkyl group, a lower alkoxy group, a methylenedioxy group and a halogen atom or a phenyl group which may optionally be substituted by at least one member selected from the group consisting of a lower alkyl group, a lower alkoxy group, a trifluoromethyl group, a nitro group, a cyano group, an amino group, a mono-lower-alkylamino group, a di-lower-alkylamino group, an acetylamino group, a benzoylamino group, a methylenedioxy group and a halogen atom, and A represents a hexamethylene group which may optionally be substituted by one or two alkyl groups having from 1 to 3 carbon atoms.

DESCRIPTION OF THE PREFERRED EMBODIMENT

The derivatives of the present invention [I] also include the tautomers of the following general formula [II]:

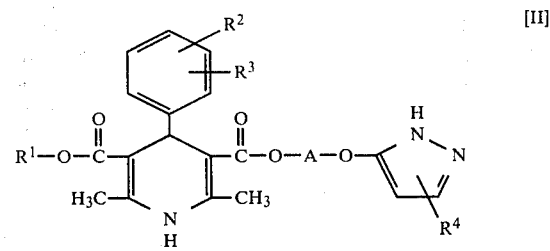

[II]

wherein $R^1$, $R^2$, $R^3$, $R^4$ and A are as defined above, as well as the optical isomers due to the asymmetric carbon atom at the 4-position of the 1,4-dihydropyridine ring.

In the definition of the general formula [I], the term "lower alkyl" means either of methyl, ethyl or propyl, and the term "halogen atom" means either atom of fluorine, chlorine, bromine or iodine, unless otherwise stated. And, of course, the terms "alkyl" and "alkoxyalkyl" include those of both straight chains and branched chains.

The derivatives of the present invention [I] may be produced by any of the processes described hereinbelow.

[Process 1]

The derivatives of the present invention [I] may be produced by reacting 1.0 mole of a benzylideneacetoacetate derivative of the following general formula [III]:

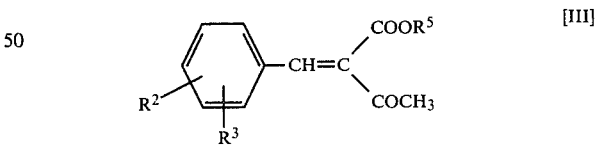

[III]

wherein $R^2$ and $R^3$ are as defined above, and $R^5$ represents $R^1$ as defined above or a substituted pyrazolyloxyhexyl group of the following general formula [IV]:

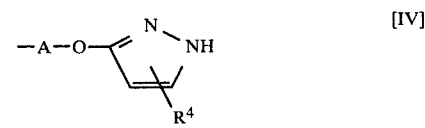

[IV]

wherein A and $R^4$ are as defined above, with 1.0–2.0 mole, preferably 1.0 mole, of an enaminocarboxylate derivative of the following general formula [V]:

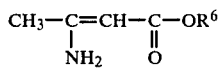

wherein $R^6$ represents $R^1$ as defined above or a substituted pyrazolyloxyhexyl group of the above general formula [IV], with a proviso that when $R^5$ is $R^1$, $R^6$ is then a substituted pyrazolyloxyhexyl group [IV], and when $R^5$ is a substituted pyrazolyloxyhexyl group [IV], $R^6$ is then $R^1$, in the presence or absence of a reaction solvent at a reaction temperature of 5°–200° C., preferably 50°–150° C. Preferred as the reaction solvent are alcohols such as methanol, ethanol, isopropanol, butanol etc., diols such as ethylene glycol, propylene glycol etc., cellosolves such as methyl cellosolve, ethyl cellosolve, propyl cellosolve etc., nitrobenzene, N,N-dimethylacetamide, N,N-dimethylformamide, hexamethylphosphoric triamide, acetic acid, water and a mixture of two or more thereof. In the above Process 1, according to the necessity, an appropriate amount of e.g. molecular sieves, piperidine, diethylamine, triethylamine, N,N-dimethylaniline, N,N-diethylaniline etc. may be employed as a reaction accelerator.

[Process 2]

The derivatives of the present invention [I] may also be produced by reacting 1.0 mole of a benzaldehyde derivative of the following general formula [VI]:

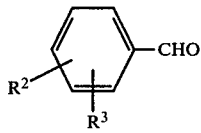

wherein $R^2$ and $R^3$ are as defined above, with 1.0–2.0 mole, preferably 1.0 mole, of an enaminocarboxylate derivative of the above general formula [V] and 1.0–2.0 mole, preferably 1.0 mole, of an acetoacetate derivative of the following general formula [VII]:

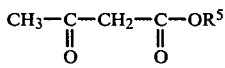

wherein $R^5$ is as defined above, in the presence or absence of a reaction solvent at a reaction temperature of 5°–200° C., preferably 50°–150° C. As the reaction solvent and the optionally employed reaction accelerator, those described in Process 1 may be employed.

[Process 3]

Further, the derivatives of the present invention [I] may also be produced by reacting 1.0 mole of a benzylideneacetoacetate derivative of the above general formula [III] with 1.0 mole of an acetoacetate derivative of the following general formula [VIII]:

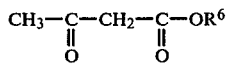

wherein $R^6$ is as defined above and 1.0 mole or more, preferably 1.0–3.0 mole, of ammonia in the presence or absence of a reaction solvent at a reaction temperature of 5°–200° C., preferably 50°–150° C. As the reaction solvent and the optionally employed reaction accelerator, those described in Process 1 may be employed.

[Process 4]

Furthermore, the derivatives of the present invention [I] may also be produced by reacting 1.0 mole of a dihydropyridine derivative of the following general formula [IX]:

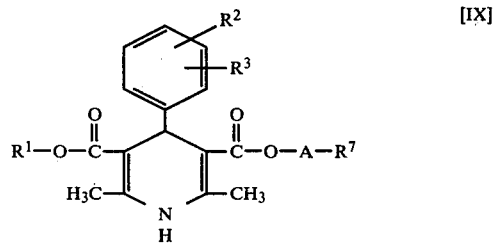

wherein $R^1$, $R^2$, $R^3$ and A are as defined above, and $R^7$ represents a halogen atom, a mesyloxy group, a tosyloxy group or a benzenesulfonyloxy group, with 1.0–6.0 moles, preferably 1.0–2.0 mole, of a pyrazolone derivative of the following general formula [X]:

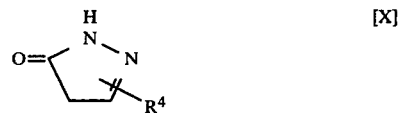

wherein $R^4$ is as defined above in the presence of an anionizing reagent and, according to the necessity, an alkali metal iodide in a reaction solvent at a reaction temperature of 0°–180° C., preferably 15°–100° C. The reaction of this Process 4 advantageously proceeds by reacting first the pyrazolone derivative [X] with the anionizing agent, and adding to the resultant reaction mixture the dihydropyridine derivative [IX] and also, according to the necessity, the alkali metal iodide.

Suitable as the anionizing reagent are alkaline metals such as metallic sodium, metallic potassium etc., alkaline earth metals such as metallic calcium, metallic magnesium etc., alkali metal hydrides such as sodium hydride, potassium hydride, lithium hydride etc., carbonates such as sodium carbonate, potassium carbonate etc., sodium or potassium alkoxides with alcohols such as methanol, ethanol, propanol, butanol etc., tertiary amines such as triethylamine, pyridine, N,N-dimethylaniline etc. When a sodium or potassium alkoxide is employed as the anionizing reagent, it is advantageous to remove as much as possible alcohol produced in the course of the reaction. In the present process, the amount of the anionizing reagent, when said reagent is other than tertiary amine, is suitably such that it falls within 1.0–6.0 mole, preferably 1.0–2.0 mole, and further that, within such a limit, it is always equimolar to or less than that of the pyrazolone derivative [X]. On the other hand, where a tertiary amine is employed, it is suitably 1.0 mole or more. The alkali metal iodide promotes the reaction of the present process where a dihydropyridine derivative in which $R^7$ in the above general formula [IX] is a halogen atom other than iodine atom is employed.

Suitable as the reaction solvent is dimethylsulfoxide, N,N-dimethylacetamide, N,N-dimethylformamide, pyridine, dioxane, hexamethylphosphoric triamide, N-methylmorpholine, 1,2-dimethoxyethane or a mixture of two or more thereof.

Furthermore, in Process 4, a compound of the following general formula [XI]:

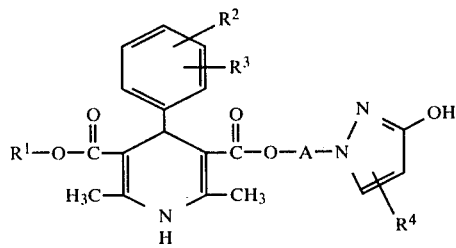

wherein $R^1$, $R^2$, $R^3$, $R^4$ and A are as defined above, may also be produced as a by-product, the compound having long-lasting hypotensive effect and vasodilating effect.

[Processes for Producing Main Starting Materials in Processes 1-4]

The acetoacetate derivatives of the above general formulae [VII] and [VIII] may be produced by using diketene and an alcohol of the following general formula [XII]:

$$R^1-OH \qquad [XII]$$

wherein $R^1$ is as defined above, or a pyrazolyloxy hexanol derivative of the following general formula [XIII]:

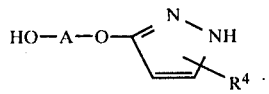

wherein $R^4$ and A are as defined above, by a process according to the known processes for producing acetoacetate derivatives, for example, the process described in the Journal of the Chemical Society, Vol. 97, p. 1978 (1910).

Secondly, the enaminocarboxylate derivative of the above general formula [V] may be produced by using the acetoacetate derivative [VIII] and ammonia by a process according to the known processes for producing enaminocarboxylate derivatives, for example, the process described in the Journal of the American Chemical Society, Vol. 67, p. 1017 (1945).

Further, the benzylideneacetoacetate derivative of the above general formula [III] may be produced by using the benzaldehyde derivative [VI] and the acetoacetate derivative [VII] by a process according to the known processes for producing benzylideneacetoacetate derivatives, for example, the process described in Organic Synthesis Collective Volume, Vol. 4, p. 408 (1963).

While in the above Processes 1-4, the explanation has been made by referring the amount of each starting compound employed to as the unit amount, i.e. 1.0 mole, for convenience sake, it is needless to say that said amount employed may be freely established as long as the relative molar ratio between the respective compounds is within the specified limit.

The derivatives of the present invention [I] produced by Processes 1-4 may be purified by such purifying method as extraction with an appropriate solvent, column chromatography using alumina, silica gel, ion exchange resin etc. as a carrier, crystallization by concentration etc., fractional precipitation, recrystallization, on an appropriate combination of these.

Test examples of the pharmacological activity of representative compounds, of the derivatives of the present invention [I], which have been produced by the above-described processes are given below.

[Hypotensive Effect]

The test was carried out using groups of 5-6 adult dogs in each group and measuring the heart rate and the blood pressure at the right femoral artery as well as the duration of the hypotensive effect after injecting 3 μg/kg or 10 μg/kg of each compound to the femoral vein. The dogs used had been anesthetized beforehand by intravenous administration of 30 mg/kg of sodium pentobarbital. The measuring instruments were a pressure transducer MPU-0.5 and a pulse rate tachometer RT-2 (both manufactured by Nippon Koden Co.), and the recording apparatus was a pen oscillograph WI-380 (manufactured by Nippon Koden Co.). The duration was obtained by measuring the time from when the effect manifested to when it died out. Administration of each compound was carried out by injecting each compound dissolved in 10% polyethylene glycol aqueous solution into the femoral vein.

The results are as set forth in Table 1. The heart rate and the hypotensive effect are expressed as the increase or decrease of the heart rate (per minute) and the difference in mean blood pressure, respectively, before and after administration of each compound, and the duration is expressed in the unit of minutes. In addition, these effects of Nifedipine and Nicardipine measured by the present inventors are also set forth in the same table.

TABLE 1

| Compound | Dosage μg/kg i.v. | Heart Rate ΔHeart Rate/ min. ± S.E. | Hypotensive Effect Mean Blood Pressure ΔmmHg ± S.E. | Duration min. ± S.E. |
|---|---|---|---|---|
| Nifedipine | 3 | 5.1 ± 0.6 | −20.1 ± 1.4 | 19.0 ± 1.3 |
|  | 10 | 9.0 ± 1.2 | −43.0 ± 3.9 | 40.6 ± 3.3 |
| Nicardipine | 3 | 19.0 ± 3.5 | −13.3 ± 2.5 | 20.1 ± 5.0 |
|  | 10 | 23.0 ± 4.5 | −23.5 ± 2.8 | 32.5 ± 6.9 |
| 1,4-Dihydro-2,6-dimethyl-4-(3-nitrophenyl)-3-methoxycarbonylpyridine-5-carboxylic acid 6-(5-phenyl-3-pyrazolyloxy)hexyl ester (Example 1) | 3 | 4.3 ± 0.8 | −12.9 ± 2.1 | 151.0 ± 5.9 |
|  | 10 | 9.2 ± 1.2 | −27.0 ± 2.6 | 180 or longer |
| 1,4-Dihydro-2,6-dimethyl-4-(3-nitrophenyl)-3-methoxycarbonylpyridine-5-carboxylic acid 6-(5-m-fluorophenyl-3-pyrazolyloxy)hexyl ester (Example 2) | 3 | 4.1 ± 1.7 | −13.2 ± 2.2 | 50.3 ± 3.8 |
|  | 10 | 8.5 ± 2.4 | −22.6 ± 1.9 | 103.5 ± 4.9 |
| 1,4-Dihydro-2,6-dimethyl-4-(2-nitrophenyl)-3-methoxycarbonylpyridine-5-carboxylic acid 6-(5-phenyl-3-pyrazolyloxy)hexyl ester (Example 3) | 3 | 2.9 ± 1.3 | −14.5 ± 1.6 | 113.2 ± 7.5 |
|  | 10 | 9.8 ± 2.9 | −25.9 ± 2.4 | 180 or longer |

TABLE 1-continued

|  |  |  | Hypotensive Effect | |
|---|---|---|---|---|
| Compound | Dosage µg/kg i.v. | Heart Rate ΔHeart Rate/ min. ± S.E. | Mean Blood Pressure ΔmmHg ± S.E. | Duration min. ± S.E. |
| 1,4-Dihydro-2,6-dimethyl-4-(3-nitrophenyl)-3-methoxycarbonylpyridine-5-carboxylic acid 6-(4-phenyl-3-pyrazolyloxy)hexyl ester (Example 9) | 3 10 | 7.3 ± 1.6 13.6 ± 2.8 | −14.7 ± 1.8 −25.2 ± 1.7 | 63.5 ± 3.8 115.6 ± 5.7 |
| 1,4-Dihydro-2,6-dimethyl-4-(3-nitrophenyl)-3-methoxycarbonylpyridine-5-carboxylic acid 6-(5-o-chlorophenyl-3-pyrazolyloxy)hexyl ester (Example 10) | 3 10 | −2.0 ± 1.3 −7.0 ± 1.8 | −14.2 ± 2.6 −20.9 ± 2.7 | 87.3 ± 4.6 180 or longer |
| 1,4-Dihydro-2,6-dimethyl-4-(2-nitrophenyl)-3-methoxycarbonylpyridine-5-carboxylic acid 6-(5-o-chlorophenyl-3-pyrazolyloxy)hexyl ester (Example 11) | 3 10 | −5.6 ± 2.5 −10.1 ± 3.0 | −21.7 ± 2.1 −37.8 ± 3.2 | 136.3 ± 9.2 180 or longer |
| 1,4-Dihydro-2,6-dimethyl-4-(3-nitrophenyl)-3-normalpropoxycarbonylpyridine-5-carboxylic acid 6-[5-(2,4-dichlorophenyl)-3-pyrazolyloxy]hexyl ester (Example 17) | 3 10 | 1.5 ± 0.3 −4.1 ± 2.7 | −10.9 ± 1.4 −18.6 ± 2.3 | 102.4 ± 7.5 159.6 ± 4.8 |
| 1,4-Dihydro-2,6-dimethyl-4-(3-nitrophenyl)-3-methoxycarbonylpyridine-5-carboxylic acid 6-(5-o-methoxyphenyl-3-pyrazolyloxy)hexyl ester (Example 19) | 3 10 | 2.0 ± 1.1 2.8 ± 1.9 | −15.7 ± 1.8 −25.3 ± 2.7 | 34.0 ± 3.6 89.5 ± 3.8 |
| 1,4-Dihydro-2,6-dimethyl-4-(3-nitrophenyl)-3-methoxycarbonylpyridine-5-carboxylic acid 6-(5-o-nitrophenyl-3-pyrazolyloxy)-3,4-dimethylhexyl ester (Example 28) | 3 10 | 4.2 ± 1.8 9.5 ± 2.7 | −16.6 ± 1.6 −28.2 ± 2.4 | 146.6 ± 4.3 180 or longer |
| 1,4-Dihydro-2,6-dimethyl-4-(3-nitrophenyl)-3-isobutoxycarbonylpyridine-5-carboxylic acid 6-(5-m-fluorophenyl-3-pyrazolyloxy)hexyl ester (Example 32) | 3 10 | 10.3 ± 2.3 16.4 ± 4.3 | −14.6 ± 1.3 −22.4 ± 2.1 | 52.1 ± 2.0 82.5 ± 4.8 |
| 1,4-Dihydro-2,6-dimethyl-4-(3-nitrophenyl)-3-(2-isobutoxyethoxycarbonyl)pyridine-5-carboxylic acid 6-(5-m-fluorophenyl-3-pyrazolyloxy)hexyl ester (Example 33) | 3 10 | 8.8 ± 3.6 10.3 ± 3.3 | −19.5 ± 1.4 −29.9 ± 2.2 | 57.2 ± 4.6 98.0 ± 5.2 |
| 1,4-Dihydro-2,6-dimethyl-4-(3-nitrophenyl)-3-methoxycarbonylpyridine-5-carboxylic acid 6-(5-o-tolyl-3-pyrazolyloxy)hexyl ester (Example 35) | 3 10 | 0.0 ± 0.0 −2.3 ± 1.1 | −12.6 ± 2.0 −21.0 ± 2.1 | 124.4 ± 7.4 180 or longer |
| 1,4-Dihydro-2,6-dimethyl-4-(3-nitrophenyl)-3-(2-isopropoxyethoxycarbonyl)pyridine-5-carboxylic acid 6-(5-o-tolyl-3-pyrazolyloxy)hexyl ester (Example 36) | 3 10 | 1.0 ± 0.3 −2.0 ± 0.8 | −13.8 ± 1.7 −25.2 ± 2.0 | 102.8 ± 4.7 165.0 ± 6.5 |
| 1,4-Dihydro-2,6-dimethyl-4-(3-nitrophenyl)-3-methoxycarbonylpyridine-5-carboxylic acid 6-(5-m-cyanophenyl-3-pyrazolyloxy)hexyl ester (Example 39) | 3 10 | 5.8 ± 2.6 8.9 ± 3.4 | −12.9 ± 1.6 −21.4 ± 1.9 | 60.8 ± 2.9 96.3 ± 4.3 |
| 1,4-Dihydro-2,6-dimethyl-4-(2-nitrophenyl)-3-methoxycarbonylpyridine-5-carboxylic acid 6-[5-(o-trifluoromethylphenyl)-3-pyrazolyloxy]hexyl ester (Example 41) | 3 10 | 7.7 ± 4.8 12.1 ± 5.3 | −20.1 ± 1.3 −32.5 ± 2.7 | 160.2 ± 7.7 180 or longer |
| 1,4-Dihydro-2,6-dimethyl-4-(3-nitrophenyl)-3-methoxycarbonylpyridine-5-carboxylic acid 6-[5-(2-pyridyl)-3-pyrazolyloxy]hexyl ester (Example 43) | 3 10 | 2.4 ± 0.8 7.8 ± 3.1 | −23.6 ± 2.1 −44.3 ± 3.4 | 48.5 ± 2.4 93.7 ± 5.8 |
| 1,4-Dihydro-2,6-dimethyl-4-(3-nitrophenyl)-3-methoxycarbonylpyridine-5-carboxylic acid 6-(5-benzyl-3-pyrazolyloxy)hexyl ester (Example 46) | 3 10 | 1.5 ± 2.4 −3.0 ± 4.2 | −14.3 ± 1.8 −22.6 ± 2.7 | 132.8 ± 9.3 180 or longer |
| 1,4-Dihydro-2,6-dimethyl-4-(3-nitrophenyl)-3-methoxycarbonylpyridine-5-carboxylic acid 6-(5-p-chlorophenyl-3-pyrazolyloxy)hexyl ester (Example 48) | 3 10 | 0.0 ± 0.0 −1.0 ± 2.0 | −14.5 ± 1.6 −25.0 ± 2.3 | 76.8 ± 2.8 137.2 ± 4.1 |
| 1,4-Dihydro-2,6-dimethyl-4-(3-nitrophenyl)-3-methoxycarbonylpyridine-5-carboxylic acid 6-(5-p-chlorophenyl-3-pyrazolyloxy)hexyl ester (Example 49) | 3 10 | 0.0 ± 0.0 −1.0 ± 0.8 | −13.8 ± 1.8 −24.3 ± 2.2 | 78.6 ± 3.6 129.0 ± 5.0 |
| 1,4-Dihydro-2,6-dimethyl-4-(3-nitrophenyl)-3-methoxycarbonylpyridine-5-carboxylic acid 6-[5-(3,4-methylenedioxyphenyl)-3-pyrazolyloxy]hexyl ester (Example 50) | 3 10 | 1.8 ± 0.9 2.4 ± 1.2 | −13.5 ± 2.4 −23.7 ± 2.6 | 58.6 ± 3.5 104.3 ± 5.2 |
| 1,4-Dihydro-2,6-dimethyl-4-(2,3-dichlorophenyl)-3-methoxycarbonylpyridine-5-carboxylic acid 6-(5-phenyl-3-pyrazolyloxy)hexyl ester (Example 52) | 3 10 | 1.5 ± 0.8 3.1 ± 1.2 | −14.5 ± 1.5 −22.8 ± 2.1 | 124.7 ± 7.3 180 or longer |
| 1,4-Dihydro-2,6-dimethyl-4-(3-nitrophenyl)-3-ethoxycarbonylpyridine-5-carboxylic acid 6-(5-o-chlorophenyl-3-pyrazolyloxy)hexyl ester (Example 53) | 3 10 | 2.0 ± 4.2 −5.3 ± 1.8 | −17.2 ± 2.2 −26.7 ± 2.4 | 98.6 ± 3.8 180 or longer |
| 1,4-Dihydro-2,6-dimethyl-4-(3-nitrophenyl)-3-methoxycarbonylpyridine-5-carboxylic acid 6-[5- | 3 10 | 1.2 ± 0.8 −1.5 ± 2.9 | −13.2 ± 1.7 −24.8 ± 2.3 | 51.2 ± 2.9 106.8 ± 3.5 |

TABLE 1-continued

| Compound | Dosage μg/kg i.v. | Heart Rate ΔHeart Rate/ min. ± S.E. | Hypotensive Effect | |
| --- | --- | --- | --- | --- |
| | | | Mean Blood Pressure ΔmmHg ± S.E. | Duration min. ± S.E. |
| (p-N—acetylaminophenyl)-3-pyrazolyloxy]hexyl ester (Example 62) | | | | |
| 1,4-Dihydro-2,6-dimethyl-4-(3-nitrophenyl)-3-ethoxycarbonylpyridine-5-carboxylic acid 6-(5-phenyl-3-pyrazolyloxy)hexyl ester (Example 65) | 3 10 | 9.3 ± 3.7 15.7 ± 2.3 | −19.5 ± 2.1 −31.2 ± 2.7 | 98.2 ± 6.2 156.1 ± 5.7 |
| 1,4-Dihydro-2,6-dimethyl-4-(2,3-dichlorophenyl)-3-methoxycarbonylpyridine-5-carboxylic acid 6-(5-p-methoxyphenyl-3-pyrazolyloxy)hexyl ester (Example 69) | 3 10 | 1.5 ± 0.8 2.6 ± 1.3 | −12.4 ± 1.7 −25.6 ± 2.3 | 80.1 ± 4.2 145.2 ± 4.6 |

As is clear from Table 1, it is observed with each compound that a hypotensive effect is retained for from about 1.5 hours in even the shortest case to as long as 3 hours or longer in the longer cases at an amount equivalent to the dosage, for example, 10 μg/kg, and that the change in heart rate is slight. In the test separately conducted on the hypotensive effect on the vertebral artery, each compound was observed to have a long-lasting vasodilating effect. Further, in the toxicity test, it was confirmed that each compound is of only a low degree of toxicity. Therefore, the derivatives of the present invention [I] are useful as drugs for treating hypertension.

The present invention is more particularly described by the following Examples.

EXAMPLE 1

4.98 g (20 mmole) of methyl 3-nitrobenzylideneacetoacetate, 6.86 g (20 mmole) of 3-aminocrotonic acid 6-(5-phenyl-3-pyrazolyloxy)hexyl ester and 7 ml of ethanol were mixed and heated at reflux for 5 hours. The reaction mixture was concentrated under reduced pressure to obtain a yellow oily residue. This oily residue was chromatographed on a silica gel column using a mixed solution of chloroform-methanol (the ratio by volume of 160:1) as an eluent and the eluate fractions containing the intended compound were concentrated under reduced pressure to obtain a yellow oil, to which was added 10 ml of ethanol, and the mixture was allowed to stand overnight, when pale yellow crystals separated. These crystals were filtered off, and recrystallized from ethanol to obtain 7.35 g (yield 64.0%) of pale yellow crystals of the 1,4-dihydro-2,6-dimethyl-4-(3-nitrophenyl)-3-methoxycarbonylpyridine-5-carboxylic acid 6-(5-phenyl-3-pyrazolyloxy)hexyl ester.

Melting point: 151°–153° C.

IR Spectrum (CHCl$_3$) cm$^{-1}$: 3500, 3460, 1695, 1520, 1345.

PMR Spectrum (CDCl$_3$) δ: 0.95–1.90(8H,m), 2.31(6H,s), 3.59(3H,s), 3.80–4.23(4H,m), 5.05(1H,s), 5.89(1H,s), 6.78(1H,s), 7.03–8.25(10H,m).

EXAMPLE 2

4.98 g (20 mmole) of methyl 3-nitrobenzylideneacetoacetate, 7.23 g (20 mmole) of 3-aminocrotonic acid 6-(5-m-fluorophenyl-3-pyrazolyloxy)hexyl ester and 10 ml of isopropanol were mixed and heated at reflux for 3 hours. This reaction mixture was concentrated under reduced pressure to obtain a yellow oily residue. This oil was purified by chromatography on a silica gel column using a mixed solution of benzene-ethyl acetate (the ratio by volume of 3:1) as an eluent to obtain eluate fractions containing the intended compound, which were concentrated to dryness under reduced pressure to obtain 6.52 g (yield 55.0%) of the 1,4-dihydro-2,6-dimethyl-4-(3-nitrophenyl)-3-methoxycarbonylpyridine-5-carboxylic acid 6-(5-m-fluorophenyl-3-pyrazolyloxy)hexyl ester as a pale yellow powder.

IR Spectrum (CHCl$_3$) cm$^{-1}$: 3500, 3460, 1693, 1520, 1345.

PMR Spectrum (CDCl$_3$+D$_2$O) δ: 1.00–1.90(8H,m), 2.33(6H,s), 3.57(3H,s), 3.76–4.21(4H,m), 5.04(1H,s), 5.87(1H,s), 7.00–8.10(8H,m).

Analysis for C$_{31}$H$_{33}$FN$_4$O$_7$: Calcd. (%): C, 62.83 H, 5.61 N, 9.45. Found (%): C, 62.91 H, 5.83 N, 9.26.

The compounds in Examples 3–47 below were producted similar procedures as in the above Example 2 except that the starting materials, the reaction solvent and other conditions were appropriately changed.

EXAMPLE 3

1,4-Dihydro-2,6-dimethyl-4-(2-nitrophenyl)-3-methoxycarbonylpyridine-5-carboxylic acid 6-(5-phenyl-3-pyrazolyloxy)hexyl ester Aspect: Pale yellow crystals.

Melting point: 198°–201° C. (from toluene).

IR Spectrum (KBr) cm$^{-1}$: 3320, 2950, 1690, 1520, 1350, 1210.

PMR Spectrum (DMSO-d$_6$) δ: 0.90–1.90(8H,m), 2.23(3H,s), 2.29(3H,s), 3.42(3H,s), 3.89(2H,t), 4.00(2H,t), 5.53(1H,s), 6.04(1H,s), 6.96–7.81(9H,m), 8.84(1H,s).

Analysis for C$_{31}$H$_{34}$N$_4$O$_7$: Calcd. (%): C, 64.80 H, 5.96 N, 9.75. Found (%): C, 64.67 H, 6.09 N, 9.59.

EXAMPLE 4

1,4-Dihydro-2,6-dimethyl-4-(3-nitrophenyl)-3-methoxycarbonylpyridine-5-carboxylic acid 6-(5-phenyl-3-pyrazolyloxy)-1,6-dimethylhexyl ester Aspect: Pale yellow powder.

IR Spectrum (CHCl$_3$) cm$^{-1}$: 3500, 3465, 1693, 1522, 1345.

PMR Spectrum (CDCl$_3$) δ: 0.81–2.00(14H,m), 2.30(6H,s), 3.56(3H,s), 5.04(1H,s), 5.89(1H,s), 6.89(1H,s).

Analysis for C$_{33}$H$_{38}$N$_4$O$_7$: Calcd. (%): C, 65.77 H, 6.36 N, 9.30. Found (%): C, 65.83 H, 6.70 N, 9.13.

EXAMPLE 5

1,4-Dihydro-2,6-dimethyl-4-(3-nitrophenyl)-3-methoxycarbonylpyridine-5-carboxylic acid 6-(5-phenyl-3-pyrazolyloxy)-6-isopropylhexyl ester Aspect: Pale yellow oil.

IR Spectrum (CHCl$_3$) cm$^{-1}$: 3500, 3460, 1690, 1520, 1345.

PMR Spectrum (CDCl$_3$) δ: 2.28(6H,s, 2,6-dimethyl group on dihydropyridine ring), 3.56(3H,s, methyl ester), 3.97(2H,t), 5.06(1H,s), 5.89(1H,s), 6.85(1H, broad).

Analysis for C$_{34}$H$_{40}$N$_4$O$_7$: Calcd. (%): C, 66.22 H, 6.54 N, 9.08. Found (%): C, 66.50 H, 6.73 N, 8.88.

EXAMPLE 6

1,4-Dihydro-2,6-dimethyl-4-(2-nitrophenyl)-3-ethoxycarbonylpyridine-5-carboxylic acid 6-(5-phenyl-3-pyrazolyloxy)hexyl ester Aspect: Pale yellow powder.

IR Spectrum (CHCl$_3$) cm$^{-1}$: 3500, 3465, 1695, 1522, 1350.

PMR Spectrum (DMSO-d$_6$) δ: 0.95–1.90(11H,m), 2.22(3H,s), 2.28(3H,s), 3.71–4.23(6H,m), 5.52(1H,s), 6.04(1H,s).

Analysis for C$_{32}$H$_{36}$N$_4$O$_7$: Calcd. (%): C, 65.29 H, 6.16 N, 9.52. Found: (%): C, 65.49 H, 6.03 N, 9.37.

EXAMPLE 7

1,4-Dihydro-2,6-dimethyl-4-(3-nitrophenyl)-3-isopropoxycarbonylpyridine-5-carboxylic acid 6-(5-phenyl-3-pyrazolyloxy)hexyl ester Aspect: Pale yellow crystals.

Melting point: 157°–160° C. (from toluene).

IR Spectrum (CHCl$_3$) cm$^{-1}$: 3500, 3460, 1693, 1520, 1345.

PMR Spectrum (CDCl$_3$) δ: 0.95–1.90(14H,m), 2.32(6H,s), 3.76–4.23(4H,m), 4.61–5.07(1H,m), 5.05(1H,s), 5.89(1H,s), 6.80(1H, broad).

Analysis for C$_{33}$H$_{38}$N$_4$O$_7$: Calcd. (%): C, 65.77 H, 6.36 N, 9.30. Found (%): C, 65.55 H, 6.42 N, 9.60.

EXAMPLE 8

1,4-Dihydro-2,6-dimethyl-4-(3-nitrophenyl)-3-(2-methoxyethoxycarbonyl)pyridine-5-carboxylic acid 6-(5-phenyl-3-pyrazolyloxy)hexyl ester Aspect: Pale yellow crystals.

Melting point: 161°–164° C. (from ethanol).

IR Spectrum (CHCl$_3$) cm$^{-1}$: 3500, 3460, 1695, 1520, 1345.

PMR Spectrum (CDCl$_3$+DMSO-d$_6$) δ: 1.00–1.87(8H,m), 2.31(6H,s), 3.27(3H,s), 3.31–3.67(2H,m), 3.73–4.28(6H,m), 5.04(1H,s), 5.86(1H,s), 7.00–8.07(9H,m).

Analysis for C$_{33}$H$_{38}$N$_4$O$_8$: Calcd. (%): C, 64.07 H, 6.19 N, 9.06. Found (%): C, 64.20 H, 6.27 N, 8.89.

EXAMPLE 9

1,4-Dihydro-2,6-dimethyl-4-(3-nitrophenyl)-3-methoxycarbonylpyridine-5-carboxylic acid 6-(4-phenyl-3-pyrazolyloxy)hexyl ester Aspect: Yellow powder.

IR Spectrum (CHCl$_3$) cm$^{-1}$: 3500, 3460, 1695, 1520, 1345.

PMR Spectrum (CDCl$_3$) δ: 0.96–1.97(8H,m), 2.30(6H,s), 3.56(3H,s), 3.68–4.20(4H,m), 5.04(1H,s), 6.80(1H, broad), 7.00–8.10(9H,m).

Analysis for C$_{31}$H$_{34}$N$_4$O$_7$: Calcd. (%): C, 64.80 H, 5.96 N, 9.75. Found (%): C, 64.93 H, 6.20 N, 9.66.

EXAMPLE 10

1,4-Dihydro-2,6-dimethyl-4-(3-nitrophenyl)-3-methoxycarbonylpyridine-5-carboxylic acid 6-(5-o-chlorophenyl-3-pyrazolyloxy)hexyl ester Aspect: Yellow crystals.

Melting point: 159°–161° C. (from ethanol).

IR Spectrum (KBr) cm$^{-1}$: 3360, 1700, 1520, 1340, 1207.

PMR Spectrum (DMSO-d$_6$) δ: 1.00–1.90(8H,m), 2.29(6H,s), 3.53(3H,s), 3.97(2H,t), 4.05(2H,t), 4.99(1H,s), 6.00(1H,s), 7.10–8.05(8H,m), 8.93(1H,s).

Analysis for C$_{31}$H$_{33}$ClN$_4$O$_7$: Calcd. (%): C, 61.13 H, 5.46 N, 9.20. Found (%): C, 61.38 H, 5.61 N, 8.92.

EXAMPLE 11

1,4-Dihydro-2,6-dimethyl-4-(2-nitrophenyl)-3-methoxycarbonylpyridine-5-carboxylic acid 6-(5-o-chlorophenyl-3-pyrazolyloxy)hexyl ester Aspect: Pale yellow crystals.

Melting point: 189°–192° C. (from ethanol).

IR Spectrum (KBr) cm$^{-1}$: 3450, 1685, 1522, 1350, 1210.

PMR Spectrum (DMSO-d$_6$) δ: 0.93–1.86(8H,m), 2.23(3H,s), 2.30(3H,s), 3.43(3H,s), 3.90(2H,t), 4.00(2H,t), 5.55(1H,s), 6.07(1H,s), 7.13–7.77(8H,m), 8.83(1H, broad).

Analysis for C$_{31}$H$_{33}$ClN$_4$O$_7$: Calcd. (%): C, 61.13 H, 5.46 N, 9.20. Found (%): C, 61.21 H, 5.70 N, 8.89.

EXAMPLE 12

1,4-Dihydro-2,6-dimethyl-4-(3-nitrophenyl)-3-methoxycarbonylpyridine-5-carboxylic acid 6-(5-m-chlorophenyl-3-pyrazolyloxy)hexyl ester Aspect: Pale yellow crystals.

Melting point: 147°–149° C. (from ethanol).

IR Spectrum (KBr) cm$^{-1}$: 3377, 2950, 1700, 1515, 1340.

PMR Spectrum (DMSO-d$_6$) δ: 0.93–1.86(8H,m), 2.30(6H,s), 3.51(3H,s), 3.67–4.17(4H,m), 4.95(1H,s), 6.11(1H,s), 7.00–7.99(8H,m).

Analysis for C$_{31}$H$_{33}$ClN$_4$O$_7$: Calcd. (%): C, 61.13 H, 5.46 N, 9.20. Found (%): C, 61.47 H, 5.60 N, 9.02.

EXAMPLE 13

1,4-Dihydro-2,6-dimethyl-4-(3-nitrophenyl)-3-ethoxycarbonylpyridine-5-carboxylic acid 6-(5-p-chlorophenyl-3-pyrazolyloxy)-1-methylhexyl ester Aspect: Pale yellow powder.

IR Spectrum (CHCl$_3$) cm$^{-1}$: 3500, 3460, 1692, 1520, 1345.

PMR Spectrum (DMSO-d$_6$) δ: 0.87–1.96(14H,m), 2.31(6H,s), 3.72–4.20(4H,m), 4.53–5.06(2H,m), 6.07(1H,s), 7.05–8.06(8H,m), 8.94(1H,s).

Analysis for C$_{33}$H$_{37}$ClN$_4$O$_7$: Calcd. (%): C, 62.21 H, 5.85 N, 8.79. Found (%): C, 62.37 H, 6.00 N, 8.63.

EXAMPLE 14

1,4-Dihydro-2,6-dimethyl-4-(2-nitrophenyl)-3-methoxycarbonylpyridine-5-carboxylic acid 6-(5-p-chlorophenyl-3-pyrazolyloxy)hexyl ester Aspect: Pale yellow crystals.

Melting point: 192°–194° C. (from benzene)

IR Spectrum (KBr) cm$^{-1}$: 3310, 1690, 1675, 1525, 1350, 1215.

PMR Spectrum (DMSO-d$_6$) δ: 0.95–2.00(8H,m), 2.22(3H,s), 2.29(3H,s), 3.43(3H,s), 3.90(2H,s), 4.00(2H,t), 5.53(1H,s), 6.09(1H,s), 7.06–7.86(8H,m), 8.83(1H,s), 12.20(1H,s).

Analysis for C$_{31}$H$_{33}$ClN$_4$O$_7$: Calcd. (%): C, 61.13 H, 5.46 N, 9.20. Found (%): C, 61.25 H, 5.70 N, 9.23.

EXAMPLE 15

1,4-Dihydro-2,6-dimethyl-4-(3-nitrophenyl)-3-methoxycarbonylpyridine-5-carboxylic acid 6-[5-(2,6-dichlorophenyl)-3-pyrazolyloxy]hexyl ester Aspect: Pale yellow powder.

IR Spectrum (CHCl$_3$) cm$^{-1}$: 3500, 3465, 1695, 1522, 1345. PMR Spectrum (DMSO-d$_6$) δ: 0.97–1.90(8H,m), 2.27(6H,s), 3.54(3H,s), 4.99(1H,s), 6.03(1H,s), 7.00–8.05(7H,m).

Analysis for C$_{31}$H$_{32}$Cl$_2$N$_4$O$_7$: Calcd. (%): C,57.86 H,5.01 N,8.71. Found (%): C,57.64 H,5.29 N,8.63.

EXAMPLE 16

1,4-Dihydro-2,6-dimethyl-4-(2-nitrophenyl)-3-isopropoxycarbonylpyridine-5-carboxylic acid 6-(5-o-chlorophenyl-3-pyrazolyloxy)hexyl ester Aspect: Pale yellow powder.

IR Spectrum (CHCl$_3$) cm$^{-1}$: 3500, 3465, 1695, 1520, 1345.

PMR Spectrum (DMSO-d$_6$) δ: 0.95–1.90(14H,m), 3.80–4.21(4H,m), 4.57–5.05(1H,m), 5.51(1H,s), 6.00(1H,s), 7.00–8.03(8H,m).

Analysis for C$_{33}$H$_{37}$ClN$_4$O$_7$: Calcd. (%): C,62.21 H,5.85 N,8.79. Found (%): C,62.07 H,5.92 N,8.59.

EXAMPLE 17

1,4-Dihydro-2,6-dimethyl-4-(3-nitrophenyl)-3-normal-propoxycarbonylpyridine-5-carboxylic acid 6-[5-(2,4-dichlorophenyl)-3-pyrazolyloxy]hexyl ester Aspect: Pale yellow powder.

IR Spectrum (CHCl$_3$) cm$^{-1}$: 3500, 3460, 1695, 1520, 1345.

PMR Spectrum (CDCl$_3$) δ: 1.02–2.00(10H,m), 2.31(6H,s), 3.78–4.23(6H,m), 5.05(1H,s), 6.01(1H,s).

Analysis for C$_{33}$H$_{36}$Cl$_2$N$_4$O$_7$: Calcd. (%): C,59.02 H,5.40 N,8.34. Found (%): C,58.71 H,5.22 H,8.50.

EXAMPLE 18

1,4-Dihydro-2,6-dimethyl-4-(2-nitrophenyl)-3-methoxycarbonylpyridine-5-carboxylic acid 6-[5-(3,4-dichlorophenyl)-3-pyrazolyloxy]hexyl ester Aspect: Pale yellow powder.

IR Spectrum (CHCl$_3$) cm$^{-1}$: 3500, 3463, 1695, 1520, 1345.

PMR Spectrum (CDCl$_3$) δ: 0.94–1.90(8H,m), 2.22(3H,s), 2.28(3H,s), 3.53(3H,s), 3.80–4.23(4H,m), 5.67(1H,s).

Analysis for C$_{31}$H$_{32}$Cl$_2$N$_4$O$_7$: Calcd. (%): C,57.86 H,5.01 N,8.71. Found (%): C,57.69 H,5.08 N,8.54.

EXAMPLE 19

1,4-Dihydro-2,6-dimethyl-4-(3-nitrophenyl)-3-methoxycarbonylpyridine-5-carboxylic acid 6-(5-o-methoxyphenyl-3-pyrazolyloxy)hexyl ester Aspect: Pale yellow crystals.
Melting point: 154°–156° C. (from ethanol).
IR Spectrum (CHCl$_3$) cm$^{-1}$: 3380, 2950, 1690, 1520, 1345.

PMR Spectrum (DMSO-d$_6$) δ: 0.90–1.88(8H,m), 2.30(6H,s), 3.53(3H,s),3.86(3H,s), 3.38–4.17(4H,m), 4.95(1H,s), 6.03(1H,s), 6.73–8.00(8H,m), 8.80 (1H, broad).

Analysis for C$_{32}$H$_{36}$N$_4$O$_8$: Calcd. (%): C,63.56 H,6.00 N,9.27. Found (%): C,63.70 H,6.27 N,9.11.

EXAMPLE 20

1,4-Dihydro-2,6-dimethyl-4-(2,3-dichlorophenyl)-3-methoxycarbonylpyridine-5-carboxylic acid 6-(5-o-methoxyphenyl-3-pyrazolyloxy)hexyl ester Aspect: White powder.

IR Spectrum (CHCl$_3$) cm$^{-1}$: 3500, 3467, 1690, 1460.

PMR Spectrum (DMSO-d$_6$) δ: 0.85–1.90(8H,m), 2.24(6H,s), 3.48(3H,s), 3.67–4.26(4H,m), 3.87(3H,s), 5.30(1H,s), 6.03(1H,s), 6.73–8.05(7H,m), 8.73(1H,s).

Analysis for C$_{32}$H$_{35}$Cl$_2$N$_3$O$_6$: Calcd. (%): C,61.15 H,5.61 N,6.69. Found (%): C,61.18 H,5.87 N,6.54.

EXAMPLE 21

1,4-Dihydro-2,6-dimethyl-4-(3-nitrophenyl)-3-normal-propoxyethoxycarbonylpyridine-5-carboxylic acid 6-(5-o-methoxyphenyl-3-pyrazolyloxy)hexyl ester Aspect: Pale yellow powder.

IR Spectrum (CHCl$_3$) cm$^{-1}$: 3500, 3460, 1690, 1520, 1345.

PMR Spectrum (CDCl$_3$+DMSO-d$_6$) δ: 0.89(3H,t), 1.00–2.00(10H,m), 2.30(6H,s), 3.18–3.75(4H,m), 3.75–4.25(6H,m), 3.87(3H,s), 5.04(1H,s), 5.95(1H,s), 6.70–8.17(8H,m).

Analysis for C$_{36}$H$_{44}$N$_4$O$_9$: Calcd. (%): C,63.89 H,6.55 N,8.28. Found (%): C,63.98 H,6.32 N,8.41.

EXAMPLE 22

1,4-Dihydro-2,6-dimethyl-4-(2-nitrophenyl)-3-methoxycarbonylpyridine-5-carboxylic acid 6-(5-m-methoxyphenyl-3-pyrazolyloxy)hexyl ester Aspect: Pale yellow powder.

IR Spectrum (CHCl$_3$) cm$^{-1}$: 3500, 3460, 1690, 1520, 1345.

PMR Spectrum (DMSO-d$_6$) δ: 0.95–1.90(8H,m), 2.21(3H,s), 2.28(3H,s), 3.43(3H,s), 3.75–4.23(4H,m), 3.82(3H,s), 5.51(1H,s), 5.96(1H,s), 6.70–8.07(8H,m).

Analysis for C$_{32}$H$_{36}$N$_4$O$_8$: Calcd. (%): C,63.56 H,6.00 N,9.27. Found (%): C,63.48 H,5.92 N,9.40.

EXAMPLE 23

1,4-Dihydro-2,6-dimethyl-4-(3-nitrophenyl)-3-isopropoxycarbonylpyridine-5-carboxylic acid 6-(5-p-methoxyphenyl-3-pyrazolyloxy)hexyl ester Aspect: Pale yellow powder.

IR Spectrum (CHCl$_3$) cm$^{-1}$: 3500, 3460, 1695, 1520, 1345.

PMR Spectrum (DMSO-d$_6$) δ: [1.06(3H,d), 1.20(3H,d) and 0.95–1.90(8H,m); total 14H], 2.31(6H,s), 3.72(3H,s), 3.73–4.21(4H,m), 4.58–5.03(1H,m), 5.02(1H,s), 5.97(1H,s), 6.93(2H,d), 7.23–8.03(6H,m), 8.91(1H,s), 12.05(1H,s).

Analysis for C$_{34}$H$_{40}$N$_4$O$_8$: Calcd. (%): C, 64.54 H, 6.37 N, 8.86. Found (%): C, 64.63 H, 6.04 N, 8.56.

EXAMPLE 24

1,4-Dihydro-2,6-dimethyl-4-(nitrophenyl)-3-methoxycarbonylpyridine-5-carboxylic acid 6-[5-(2,3-dimethoxyphenyl)-3-pyrazolyloxy]hexyl ester Aspect: Pale yellow powder.

IR Spectrum (CHCl$_3$) cm$^{-1}$: 3500, 3460, 1693, 1522, 1345.

PMR Spectrum (CDCl$_3$) δ: 0.95–2.00(8H,m), 2.28(6H,s), 3.59(3H,s), 3.85(6H,s), 3.70–4.26(4H,m), 5.03(1H,s), 5.93(1H,s), 6.30(1H,s), 6.65–8.13(7H,m).

Analysis for $C_{33}H_{38}N_4O_9$: Calcd. (%): C,62.45 H,6.04 N,8.83. Found (%): C,62.53 H,6.27 N,8.55.

EXAMPLE 25

1,4-Dihydro-2,6-dimethyl-4-(3-nitrophenyl)-3-methoxycarbonypyridine-5-carboxylic acid 6-[5-(3,4-dimethoxyphenyl)-3-pyrazolyloxy]hexyl ester Aspect: Pale yellow powder.
IR Spectrum (CHCl$_3$) cm$^{-1}$: 3500, 3460, 1695, 1520, 1345.
PMR Spectrum (CDCl$_3$) δ: 0.96–1.90(8H,m), 2.30(6H,s), 3.56(3H,s), 3.70–4.21(4H,m), 3.88(6H,s), 5.05(1H,s), 5.85(1H,s).
Analysis for $C_{33}H_{38}N_4O_9$: Calcd. (%): C,62.45 H,6.04 N,8.83. Found (%): C,62.54 H,6.18 N,8.62.

EXAMPLE 26

1,4-Dihydro-2,6-dimethyl-4-(3-nitrophenyl)-3-ethoxycarbonylpyridine-5-carboxylic acid 6-[5-(3,4-methylenedioxyphenyl)-3-pyrazolyloxy]hexyl ester Aspect: Pale yellow powder.
IR Spectrum (CHCl$_3$) cm$^{-1}$: 3500, 3465, 1695, 1520, 1345.
PMR Spectrum (DMSO-d$_6$) δ: 0.89–1.90(8H,m), 1.16(3H,t), 2.28(6H,s), 3.73–4.23(6H,m), 4.97(1H,s), 5.95(3H,s), 6.74–8.04(7H,m), 8.97(1H, broad), 11.90(1H, broad).
Analysis for $C_{33}H_{36}N_4O_9$: Calcd. (%): C,62.65 H,5.74 N,8.86. Found (%): C,62.79 H,5.81 N,8.59.

EXAMPLE 27

1,4-Dihydro-2,6-dimethyl-4-(3-nitrophenyl)-3-methoxycarbonylpyridine-5-carboxylic acid 6-[5-(3,4,5-trimethoxyphenyl)-3-pyrazolyloxy]hexyl ester Aspect: Pale yellow powder.
IR Spectrum (CHCl$_3$) cm$^{-1}$: 3500, 3460, 1692, 1521, 1345.
PMR Spectrum (CDCl$_3$) δ: 1.00–1.95(8H,m), 2.33(6H,s), 3.61(3H,s), 3.71–4.22(4H,m), 3.79(3H,s), 3.81(6H,s),5.03(1H,s), 5.83(1H,s), 6.50(1H,s), 6.75(2H,s), 7.10–8.13(4H,m).
Analysis for $C_{34}H_{40}N_4O_{10}$: Calcd. (%): C,61.44 H,6.07 N,8.43. Found (%): C,61.21 H,6.00 N,8.56.

EXAMPLE 28

1,4-Dihydro-2,6-dimethyl-4-(3-nitrophenyl)-3-methoxycarbonylpyridine-5-carboxylic acid 6-(5-o-nitrophenyl-3-pyrazolyloxy)-3,4-dimethylhexyl ester Aspect: Pale yellow powder.
IR Spectrum (CHCl$_3$) cm$^{-1}$: 3500, 3460, 1693, 1520, 1345.
PMR Spectrum (DMSO-d$_6$) δ: 2.28(6H,s), 3.53(3H,s), 3.75–4.21(4H,m), 5.01(1H,s).
Analysis for $C_{33}H_{37}N_5O_9$: Calcd. (%): C,61.20 H,5.76 N,10.81. Found (%): C,61.53 H,5.77 N,10.60.

EXAMPLE 29

1,4-Dihydro-2,6-dimethyl-4-(3-nitrophenyl)-3-methoxycarbonylpyridine-5-carboxylic acid 6-(5-m-nitrophenyl-3-pyrazolyloxy)hexyl ester Aspect: Yellow crystals.
Melting point: 96°–99° C. (from ethanol).
IR Spectrum (KBr) cm$^{-1}$: 3440, 1690, 1520, 1342, 1210.
PMR Spectrum (DMSO-d$_6$) δ: 1.00–1.90(8H,m), 2.26(6H,s), 3.56(3H,s), 3.70–4.22(4H,m), 4.97(1H,s), 6.27(1H,s), 7.25–8.52(8H,m), 8.78(1H,s).
Analysis for $C_{31}H_{33}N_5O_9$: Calcd. (%): C,60.09 H,5.37 N,11.30. Found (%): C,60.03 H,5.48 N,11.11.

EXAMPLE 30

1,4-Dihydro-2,6-dimethyl-4-(3-nitrophenyl)-3-isopropoxycarbonylpyridine-5-carboxylic acid 6-(5-m-nitrophenyl-3-pyrazolyloxy)hexyl ester Aspect: Yellow powder.
IR Spectrum (CHCl$_3$) cm$^{-1}$: 3500, 3463, 2950, 1696, 1520.
PMR Spectrum (DMSO-d$_6$) δ: [1.07(d), 1.22(d) and 0.90–1.95(m); total 14H], 2.31(6H,s), 3.75–4.23(4H,m), 4.55–5.05(1H,m), 4.99(1H,s), 6.27(1H,s), 7.25–8.50(8H,m).
Analysis for $C_{33}H_{37}N_5O_9$: Calcd. (%): C,61.20 H,5.76 N,10.81. Found (%): C,61.26 H,5.97 N,10.63.

EXAMPLE 31

1,4-Dihydro-2,6-dimethyl-4-(3-nitrophenyl)-3-methoxycarbonylpyridine-5-carboxylic acid 6-(5-o-fluorophenyl-3-pyrazolyloxy)hexyl ester Aspect: Pale yellow glassy solid.
IR Spectrum (CHCl$_3$) cm$^{-1}$: 3500, 3460, 1695, 1520, 1345.
PMR Spectrum (CDCl$_3$) δ: 1.00–1.90(8H,m), 2.30(6H,s), 3.57(3H,s), 3.73–4.21(4H,m), 5.05(1H,s), 5.86(1H,s).
Analysis for $C_{31}H_{33}FN_4O_7$: Calcd. (%): C,62.83 H,5.61 N,9.45. Found (%): C,62.94 H,5.56 N,9.62.

EXAMPLE 32

1,4-Dihydro-2,6-dimethyl-4-(3-nitrophenyl)-3-isobutoxycarbonylpyridine-5-carboxylic acid 6-(5-m-fluorophenyl-3-pyrazolyloxy)hexyl ester Aspect: Pale yellow powder.
IR Spectrum (CHCl$_3$) cm$^{-1}$: 3500, 3460, 1695, 1520, 1345.
PMR Spectrum (CDCl$_3$) δ: 0.80(6H,dd), 1.00–2.05(9H,m), 2.28(6H,s), 3.76(2H,d), 3.74–4.22(4H,m), 5.03(1H,s), 5.85(1H,s), 6.30(1H,s), 7.00–8.13(8H,m).
Analysis for $C_{34}H_{39}FN_4O_7$: Calcd. (%): C,64.34 H,6.19 N,8.83. Found (%): C,64.08 H,6.24 N,8.99.

EXAMPLE 33

1,4-Dihydro-2,6-dimethyl-4-(3-nitrophenyl)-3-(2-isobutoxyethoxycarbonyl)pyridine-5-carboxylic acid 6-(5-m-fluorophenyl-3-pyrazolyloxy)hexyl ester Aspect: Pale yellow powder.
IR Spectrum (CHCl$_3$) cm$^{-1}$: 3500, 3460, 1695, 1520, 1345.
PMR Spectrum (CDCl$_3$) δ: 0.87(6H,d), 1.05–2.07(9H,m), 2.28(6H,s), 3.13(2H,d), 3.35–3.71(2H), 3.77–4.24(6H,m), 5.03(1H,s), 5.88(1H,s), 7.02–8.13(8H,m).
Analysis for $C_{36}H_{43}FN_4O_8$: Calcd. (%): C,63.70 H,6.39 N,8.25. Found (%): C,63.88 H,6.62 N,8.10.

EXAMPLE 34

1,4-Dihydro-2,6-dimethyl-4-(3-nitrophenyl)-3-methoxycarbonylpyridine-5-carboxylic acid 6-(5-p-fluorophenyl-3-pyrazolyloxy)hexyl ester Aspect: Pale yellow powder.
IR Spectrum (CHCl$_3$) cm$^{-1}$: 3500, 3460, 1695, 1520, 1345.
PMR Spectrum (CDCl$_3$+D$_2$O) δ: 1.00–1.90(8H,m), 2.30(6H,s), 3.56(3H,s), 3.73–4.21(4H,m), 5.03(1H,s), 6.90–8.10(8H,m).

Analysis for C$_{31}$H$_{33}$FN$_4$O$_7$: Calcd. (%): C,62.83 H,5.61 N,9.45. Found: (%): C,62.92 H,5.48 N,9.46.

EXAMPLE 35

1,4-Dihydro-2,6-dimethyl-4-(3-nitrophenyl)-3-methoxycarbonylpyridine-5-carboxylic acid 6-(5-o-tolyl-3-pyrazolyloxy)hexyl ester Aspect: Pale yellow crystals.
Melting point: 135–137° C. (from isopropanol).
IR Spectrum (KBr) cm$^{-1}$: 3360, 2950, 1702, 1520, 1342, 1210.
PMR Spectrum (DMSO-d$_6$) δ: 1.00–1.91(8H,m), 2.31(6H,s), 2.35(3H,s), 3.53(3H,s), 3.78–4.22(4H,m), 4.99(1H,s), 5.87(1H,s), 7.00–8.05(8H,m).
Analysis for C$_{32}$H$_{36}$N$_4$O$_7$: Calcd. (%): C,65.29 H,6.16 N,9.52. Found (%): C,65.38 H,6.31 N,9.27.

EXAMPLE 36

1,4-Dihydro-2,6-dimethyl-4-(3-nitrophenyl)-3-(2-isopropoxyethoxycarbonyl)pyridine-5-carboxylic acid 6-(5-o-tolyl-3-pyrazolyloxy)hexyl ester Aspect: Pale yellow powder.
IR Spectrum (CHCl$_3$) cm$^{-1}$: 3500, 3460, 1695, 1520, 1345.
PMR Spectrum (CDCl$_3$) δ: [0.94–1.90(8H,m) and 1.13(6H,d); total 14H], 2.30(6H,s), 2.34(3H,s), 3.21–4.31(9H,m), 5.04(1H,s), 5.72(1H,s), 6.48(1H,s), 7.05–8.05(8H,m).
Analysis for C$_{36}$H$_{44}$N$_4$O$_8$: Calcd. (%): C,65.44 H,6.71 N,8.48. Found (%): C,65.60 H,6.85 N,8.31.

EXAMPLE 37

1,4-Dihydro-2,6-dimethyl-4-(2-nitrophenyl)-3-methoxycarbonylpyridine-5-carboxylic acid 6-(5-o-tolyl-3-pyrazolyloxy)hexyl ester Aspect: Yellow powder.
IR Spectrum (CHCl$_3$)cm$^{-1}$: 3500, 3460, 1693, 1522, 1345.
PMR Spectrum (DMSO-d$_6$) δ: 0.95–1.97(8H,m), 2.22(3H,s), 2.29(3H,s), 2.35(3H,s), 3.45(3H,s), 3.74–4.22(4H,m), 5.51(1H,s), 5.85(1H,s), 6.96–8.10(8H,m), 8.90(1H, broad).
Analysis for C$_{32}$H$_{36}$N$_4$O$_7$: Calcd. (%): C,65.29 H,6.16 N,9.52. Found (%): C,65.03 H,6.31 N,9.49.

EXAMPLE 38

1,4-Dihydro-2,6-dimethyl-4-(2-nitrophenyl)-3-methoxycarbonylpyridine-5-carboxylic acid 6-(5-o-cyanophenyl-3-pyrazolyloxy)hexyl ester Aspect: Pale yellow powder.
IR Spectrum (CHCl$_3$) cm$^{-1}$: 3500, 3460, 2230, 1696, 1520, 1345.
PMR Spectrum (DMSO-d$_6$) δ: 0.96–1.90(8H,m), 2.20(3H,s), 2.27(3H,s), 3.43(3H,s), 3.75–4.22(4H,m), 5.52(1H,s).
Analysis for C$_{32}$H$_{33}$N$_5$O$_7$: Calcd. (%): C,64.10 H,5.55 N,11.68. Found (%): C,63.88 H,5.67 N,11.83.

EXAMPLE 39

1,4-Dihydro-2,6-dimethyl-4-(3-nitrophenyl)-3-methoxycarbonylpyridine-5-carboxylic acid 6-(5-m-cyanophenyl-3-pyrazolyloxy)hexyl ester Aspect: Pale yellow powder.
IR Spectrum (CHCl$_3$) cm$^{-1}$: 3500, 3460, 2227, 1695, 1520, 1345.
PMR Spectrum (CDCl$_3$) δ: 1.00–1.95(8H,m), 2.30(6H,s), 3.57(3H,s), 3.75–4.22(4H,m), 5.06(1H,s), 6.12(1H,s).
Analysis for C$_{32}$H$_{33}$N$_5$O$_7$: Calcd. (%): C,64.10 H,5.55 N,11.68. Found (%): C,63.87 H,5.71 N,11.49.

EXAMPLE 40

1,4-Dihydro-2,6-dimethyl-4-(3-nitrophenyl)-3-methoxycarbonylpyridine-5-carboxylic acid 6-(5-p-cyanophenyl-3-pyrazolyloxy)hexyl ester Aspect: Pale yellow powder.
IR Spectrum (CHCl$_3$) cm$^{-1}$: 3500, 3460, 2230, 1695, 1520, 1345.
PMR Spectrum (CDCl$_3$) δ: 1.00–1.92(8H,m), 2.30(6H,s), 3.57(3H,s), 3.75–4.21(4H,m), 5.03(1H,s), 5.82(1H,s), 6.10(1H,s), 7.07–8.10(8H,m).
Analysis for C$_{32}$H$_{33}$N$_5$O$_7$: Calcd. (%): C,64.10 H,5.55 N,11.68. Found (%): C,63.94 H,5.80 N,11.57.

EXAMPLE 41

1,4-Dihydro-2,6-dimethyl-4-(2-nitrophenyl)-3-methoxycarbonylpyridine-5-carboxylic acid 6-[5-(o-trifluoromethylphenyl)-3-pyrazolyloxy]hexyl ester Aspect: Pale yellow powder.
IR Spectrum (CHCl$_3$) cm$^{-1}$: 3500, 3460, 1696, 1520, 1345.
PMR Spectrum (CDCl$_3$) δ: 0.96–1.90(8H,m), 2.30(6H,s), 3.55(3H,s), 3.76–4.27(4H,m), 5.73(1H,s).
Analysis for C$_{32}$H$_{33}$F$_3$N$_4$O$_7$: Calc. (%): C,59.81 H,5.18 N,8.72. Found (%): C,59.80 H,5.34 N,8.60.

EXAMPLE 42

1,4-Dihydro-2,6-dimethyl-4-(2-nitrophenyl)-3-methoxycarbonylpyridine-5-carboxylic acid 6-[5-(m-trifluoromethylphenyl)-3-pyrazolyloxy]hexyl ester Aspect: Pale yellow powder.
IR Spectrum (CHCl$_3$) cm$^{-1}$: 3500, 3460, 1695, 1520, 1345.
PMR Spectrum (CDCl$_3$)δ: 0.93–1.90(8H,m), 2.31(6H,s), 3.56(3H,s), 3.75–4.28(4H,m), 5.75(1H,s).
Analysis for C$_{32}$H$_{33}$F$_3$N$_4$O$_7$: Calcd. (%): C,59.81 H,5.18 N,8.72. Found (%): C,59.97 H,5.32 N,8.47.

Example 43

1,4-Dihydro-2,6-dimethyl-4-(3-nitrophenyl)-3-methoxycarbonylpyridine-5-carboxylic acid 6-[5-(2-pyridyl)-3-pyrazolyloxy]hexyl ester Aspect: Pale yellow powder.
IR Spectrum (CHCl$_3$) cm$^{-1}$: 3500, 3460, 1695, 1520, 1345.
PMR Spectrum (CDCl$_3$) δ: 0.97–2.00(8H,m), 2.30(6H,s), 3.57(3H,s), 3.73–4.22(4H,m), 5.03(1H,s), 6.01(1H,s).
Analysis for C$_{30}$H$_{33}$N$_5$O$_7$: Calcd. (%): C,62.60 H,5.78 N,12.17. Found (%): C,62.26 H,5.83 N, 12.36.

EXAMPLE 44

1,4-Dihydro-2,6-dimethyl-4-(3-nitrophenyl)-3-methoxycarbonylpyridine-5-carboxylic acid 6-[5-(3-pyridyl)-3-pyrazolyloxy]hexyl ester Aspect: Pale yellow powder.
IR Spectrum (CHCl$_3$) cm$^{-1}$: 3500, 3460, 1694, 1520, 1345.
PMR Spectrum (CDCl$_3$) δ: ,s).

Analysis for $C_{30}H_{33}N_5O_7$: Calcd. (%): C,62.60 H,5.78 N,12.17. Found (%): C,62.71 H,5.80 N,12.32.

EXAMPLE 45

1,4-Dihydro-2,6-dimethyl-4-(3-nitrophenyl)-3-methoxycarbonylpyridine-5-carboxylic acid 6-[5-(4-pyridyl)-3-pyrazolyloxy]hexyl ester Aspect: Pale yellow crystals.
Melting point: 165°–168° C. (from ethanol).
IR Spectrum (CHCl$_3$) cm$^{-1}$: 3500, 3465, 1695, 1523, 1345.
PMR Spectrum (DMSO-d$_6$) δ: 1.00–1.92(8H,m), 2.30(6H,s), 3.56(3H,s), 3.77–4.24(4H,m), 5.01(1H,s), 6.36(1H,s), 7.05–8.15(6H,m), 8.48–8.74(2H,m).
Analysis for $C_{30}H_{33}N_5O_7$: Calcd. (%): C,62.60 H,5.78 N,12.17. Found (%): C,62.57 H,5.99 N,12.25.

EXAMPLE 46

1,4-Dihydro-2,6-dimethyl-4-(3-nitrophenyl)-3-methoxycarbonylpyridine-5-carboxylic acid 6-(5-benzyl-3-pyrazolyloxy)hexyl ester Aspect: Pale yellow oil.
IR Spectrum (CHCl$_3$) cm$^{-1}$: 3500, 3460, 1693, 1520, 1345.
PMR Spectrum (CDCl$_3$) δ: 0.97–2.00(8H,m), 2.31(6H,s), 3.56(3H,s), 3.85(2H,s), 3.74–4.21(4H,m), 5.08(1H,s), 5.42(1H,s), 6.62(1H,s), 7.00–8.40(10H,m).
Analysis for $C_{32}H_{36}N_4O_7$: Calcd. (%): C,65.29 H,6.16 N,9.52. Found (%): C,65.07 H,6.33 N,9.50.

EXAMPLE 47

1,4-Dihydro-2,6-dimethyl-4-(3-nitrophenyl)-3-methoxycarbonylpyridine-5-carboxylic acid 6-(5-o-chlorobenzyl-3-pyrazolyloxy)hexyl ester Aspect: Pale yellow oil.
IR Spectrum (CHCl$_3$) cm$^{-1}$: 3500, 3460, 1693, 1522, 1345.
PMR Spectrum (CDCl$_3$+D$_2$O) δ: 0.95–1.90(8H,m), 2.30(6H,s), 3.57(3H,s), 3.73–4.20(4H,m), 3.82(2H,s), 5.07(1H,s), 5.43(1H,s), 6.90–8.10(8H,m).
Analysis for $C_{32}H_{35}ClN_4O_7$: Calcd. (%): C,61.68 H,5.66 N,8.99. Found (%): C,61.60 H,5.78 N,9.14.

EXAMPLE 48

4.98 g (20 mmole) of methyl 3-nitrobenzylideneacetoacetate, 7.55 g (20 mmole) of 3-aminocrotonic acid 6-(5-p-chlorophenyl-3-pyrazolyloxy)hexyl ester and 10 ml of ethanol were mixed and heated at reflux for 6 hours. This reaction mixture was concentrated under reduced pressure to obtain a yellow oily residue, which, after adding 2 ml of ethyl acetate, was stirred overnight. Then, the separated crystals were filtered off, and recrystallized from isopropanol to obtain 8.65 g (yield 71.0%) of pale yellow crystals of the 1,4-dihydro-2,6-dimethyl-4-(3-nitrophenyl)-3-methoxycarbonylpyridine-5-carboxylic acid 6-(5-p-chlorophenyl-3-pyrazolyloxy)hexyl ester.

Melting point: 187°–188° C.
IR Spectrum (KBr) cm$^{-1}$: 3380, 1705, 1690, 1515, 1345.
PMR Spectrum (DMSO-d$_6$) δ: 1.00–1.91(8H,m), 2.31(6H,s), 3.52(3H,s), 3.77–4.20(4H,m),4.97(1H,s), 6.07(1H,s), 7.05–8.06(8H,m), 8.94(1H,s).
Analysis for $C_{31}H_{33}ClN_4O_7$: Calcd. (%): C,61.13 H,5.46 N,9.20. Found (%): C,61.33 H,5.57 N,9.02.

EXAMPLE 49

1.51 g (10 mmole) of 3-nitrobenzaldehyde, 1.15 g (10 mmole) of methyl 3-aminocrotonate, 3.74 g (10 mmole) of acetoacetic acid 6-(5-p-methoxyphenyl-3-pyrazolyloxy)hexyl ester and 20 ml of ethanol were mixed and heated at reflux for 5 hours. This reaction mixture was concentrated under reduced pressure to obtain a yellow oily residue. This residue was chromatographed on a silica gel column using chloroform as an eluent, and the purified fractions containing the intended compound were concentrated under reduced pressure to obtain yellow crystals. These crystals were recrystallized from isopropanol to obtain 1.39 g (yield 23.0%) of pale yellow crystals of the 1,4-dihydro-2,6-dimethyl-4-(3-nitrophenyl)-3-methoxycarbonylpyridine-5-carboxylic acid 6-(5-p-methoxyphenyl-3-pyrazolyloxy)hexyl ester.

Melting point: 160°–163° C.
IR Spectrum (KBr) cm$^{-1}$: 3398, 1700, 1508, 1345, 1210.
PRM Spectrum (DMSO-d$_6$) δ: 1.00–1.91(8H,m), 2.31(6H,s), 3.51(3H,s), 3.71(3H,s), 3.78–4.18(4H,m), 5.01(1H,s), 5.97(1H,s), 6.92(2H,d), 7.22–8.00(6H,m), 8.93(1H,s).
Analysis for $C_{32}H_{36}N_4O_8$: Calcd. (%): C,63.56 H,6.00 N,9.27. Found (%): C,63.68 H,6.21 N,9.15.

EXAMPLE 50

0.24 g (10 mmole) of sodium hydride was suspended in 10 ml of N,N-dimethylformamide, to which was added 2.45 g (12 mmole) of 3-(3,4-methylenedioxyphenyl)-5-pyrazolone with stirring at room temperature. After evolution of hydrogen had ceased, to this solution was added dropwise 10 ml of a solution of 5.87 g (10 mmole) of 1,4-dihydro-2,6-dimethyl-4-(3-nitrophenyl)-3-methoxycarbonylpyridine-5-carboxylic acid 6-tosyloxyhexyl ester in N,N-dimethylformamide, and the mixture was stirred and heated at 90° C. for an hour. The resultant reaction mixture was poured into 200 ml of ice water, and the separated solid was filtered off. This solid was recrystallized from ethyl acetate to obtain 3.21 g (yield 51.9%) of the 1,4-dihydro-2,6-dimethyl-4-(3-nitrophenyl)-3-methoxycarbonylpyridine-5-carboxylic acid 6-[5-(3,4-methylenedioxyphenyl)-3-pyrazolyloxy]hexyl ester.

Aspect: Pale yellow crystals.
Melting point: 167°–169° C.
IR Spectrum (KBr) cm$^{-1}$: 3380, 1694, 1520, 1345.
PMR Spectrum (DMSO-d$_6$) δ: 0.97–1.85(8H, m), 2.28(6H,s), 3.52(3H,s), 3.72–4.18(4H,m), 4.96(1H,s), 5.97(3H,s), 6.76–8.02(7H,m), 8.90(1H,s), 11.97(1H,s).
Analysis for $C_{32}H_{34}N_4O_9$: Calcd. (%): C,62.13 H,5.54 N,9.06. Found (%): C,61.85 H,5.46 N,9.29.

The compound in Example 51 below was produced similarly as in Example 50, except that the starting materials were changed.

EXAMPLE 51

1,4-Dihydro-2,6-dimethyl-4-(3-nitrophenyl)-3-methoxycarbonylpyridine-5-carboxylic acid 6-(5-p-nitrophenyl-3-pyrazolyloxy)hexyl ester Aspect: Yellow crystals.
Melting point: 208°–210° C. (from acetic acid).
IR Spectrum (KBr) cm$^{-1}$: 3425, 1696, 1505, 1340, 1208.

PMR Spectrum (DMSO-d$_6$) δ: 1.00–1.90(8H,m), 2.29(6H,s), 3.56(3H,s), 3.77–4.23(4H,m), 4.98(1H,s), 6.28(1H,s), 7.38–8.30(8H,m), 8.86(1H,s), 12.40(1H,s).

Analysis for C$_{31}$H$_{33}$N$_5$O$_9$: Calcd. (%): C,60.09 H,5.37 N,11.30. Found (%): C,60.25 H,5.54 N,11.17.

EXAMPLE 52

(Step i)

35.0 g (0.20 mole) of 2,3-dichlorobenzaldehyde, 23.0 g (0.20 mole) of methyl 3-aminocrotonate, 40.0 g (0.20 mole) of acetoacetic acid 6-hydroxyhexyl ester and 100 ml of ethanol were mixed and heated at reflux for 6 hours, and the resultant product was chromatographed on a silica gel column to obtain 34.7 g (yield 38.0%) of 1,4-dihydro-2,6-dimethyl-4-(2,3-dichlorophenyl)-3-methoxycarbonylpyridine-5-carboxylic acid 6-hydroxyhexyl ester as an oil. 13.7 g (0.03 mole) of this oil was dissolved together with 11.4 g (0.06 mole) of tosyl chloride in 100 ml of chloroform, to which was added dropwise 7.1 g (0.09 mole) of pyridine under ice cooling with stirring. This mixture was allowed to stand at room temperature for 2 hours, then 100 ml of water was added thereto, and stirring was continued for 3 hours. The chloroform layer of the resultant reaction mixture was separated, washed with 100 ml of 0.02 N sulfuric acid, 100 ml of water and 100 ml of saturated aqueous sodium bicarbonate successively, and dried over anhydrous sodium sulfate. This solution was concentrated, and the resultant residue was chromatographed on a silica gel column using a mixed solution of chloroform-methanol (the ratio by volume of 150:1) as an eluent to obtain 16.3 g (yield 89.0%) of 1,4-dihydro-2,6-dimethyl-4-(2,3-dichlorophenyl)-3-methoxycarbonylpyridine-5-carboxylic acid 6-tosyloxyhexyl ester. The IR and PMR spectra of this product were as follows.

IR Spectrum (KBr) cm$^{-1}$: 3340, 1675, 1475, 1345, 1205.

PMR Spectrum (CDCl$_3$) δ: 0.83–1.83(8H,m), 2.23(6H,s), 2.37(3H,s), 3.53(3H,s), 3.73–4.17(4H,m), 5.36(1H,s), 6.53(1H,s), 6.83–7.36(5H,m), 7.50–7.83(2H,d).

(Step ii)

0.51 g (12 mmole) of 55% sodium hydride in mineral oil was suspended in 10 ml of N,N-dimethylformamide, to which was added gradually 2.40 g (15 mmole) of 3-phenyl-5-pyrazolone with stirring at room temperature. After evolution of hydrogen had ceased, to this solution was added dropwise 20 ml of a solution of 6.10 g (10 mmole) of the 1,4-dihydro-2,6-dimethyl-4-(2,3-dichlorophenyl)-3-methoxycarbonylpyridine-5-carboxylic acid 6-tosyloxyhexyl ester obtained in the above Step i in N,N-dimethylformamide, and stirring with heating at 60° C. was continued for 4 hours. The resultant reaction mixture was poured into 150 ml of ice water, and the separated product was extracted with 50 ml of ethyl acetate. This ethyl acetate solution was washed with 50 ml of water three times, dried over anhydrous sodium sulfate, and then concentrated under reduced pressure to obtain a brown oily residue. This residue was chromatographed on a silica gel column using a chloroform-methanol mixed solution as an eluent, and the eluatefractions containing the intended compound were concentrated under reduced pressure to obtain crystals. These crystals were recrystallized from a mixed solution of benzene-hexane to obtain 2.63 g (yield 43.9%) of the 1,4-dihydro-2,6-dimethyl-4-(2,3-dichlorophenyl)-3-methoxycarbonylpyridine-5-carboxylic acid 6-(5-phenyl-3-pyrazolyloxy)hexyl ester.

Aspect: Colorless crystals.

Melting point: 68°–71° C.

IR Spectrum (CHCl$_3$) cm$^{-1}$: 3499, 3470, 1690, 1460.

PMR Spectrum (CDCl$_3$+D$_2$O) δ: 0.93–1.90(8H,m), 2.25(6H,s), 3.58(3H, s), 3.74–4.25(4H,m), 5.43(1H,s), 5.89(1H,s), 6.80–7.72(8H,m).

Analysis for C$_{31}$H$_{33}$Cl$_2$N$_3$O$_5$: Calcd. (%): C,62.21 H,5.56 N,7.02. Found (%): C,62.18 H,5.78 N,6.77.

EXAMPLE 53

0.24 g (10 mmole) of sodium hydride was suspended in 10 ml of dimethylsulfoxide, to which was added gradually 1.95 g (10 mmole) of 3-o-chlorophenyl-5-pyrazolone with stirring at room temperature. After evolution of hydrogen had ceased, to this solution was added 10 ml of a solution of 6.01 g (10 mmole) of 1,4-dihydro-2,6-dimethyl-4-(3-nitrophenyl)-3-ethoxycarbonylpyridine-5-carboxylic acid 6-tosyloxyhexyl ester in dimethylsulfoxide, and stirring with heating at 80° C. was continued for an hour. The resultant reaction mixture was poured into 150 ml of ice water, and the separated product was extracted with 50 ml of chloroform. This chloroform solution was washed with 50 ml of water 4 times, then dried over anhydrous sodium sulfate, and concentrated under reduced pressure to obtain a brown oily residue. This residue was purified by chromatography on a silica gel column using a mixed solution of chloroform-methanol (the ratio by volume of 100:1) as an eluent, and further by chromatography on a silica gel column eluting with a toluene-ethyl acetate mixed solution, and the eluate fractions containing the purified intended compound were concentrated to dryness under reduced pressure to obtain 2.55 g (yield 40.9%) of the 1,4-dihydro-2,6-dimethyl-4-(3-nitrophenyl)-3-ethoxycarbonyl-pyridine-5-carboxylic acid 6-(5-o-chlorophenyl-3-pyrazolyloxy)hexyl ester as a pale yellow powder.

IR Spectrum (CHCl$_3$) cm$^{-1}$: 3500, 3460, 1695, 1520, 1345.

PMR Spectrum (DMSO-d$_6$) δ: 0.89–1.90(8H,m), 1.16(3H,t), 2.27(6H,s), 3.73–4.21(6H,m), 5.01(1H,s), 6.01(1H,s), 7.05–8.05(8H,m), 8.83(1H, broad), 12.07(1H, broad).

Analysis for C$_{32}$H$_{35}$ClN$_4$O$_7$: Calcd. (%): C,61.68 H,5.66 N,8.99. Found (%): C,61.78 H,5.83 N,8.84.

The compounds in Examples 54–67 below were produced by similar procedures as in the above Example 53, except that the starting materials, the reaction solvent, and other conditions were appropriately changed.

EXAMPLE 54

1,4-Dihydro-2,6-dimethyl-4-(3-nitrophenyl)-3-methoxycarbonylpyridine-5-carboxylic acid 6-(5-p-trifluoromethylphenyl-3-pyrazolyloxy)hexyl ester Aspect: Pale yellow powder.

IR Spectrum (CHCl$_3$) cm$^{-1}$: 3500, 3460, 1693, 1520, 1345.

PMR Spectrum (DMSO-d$_6$) δ: 0.90–1.91(8H,m), 2.29(6H,s), 3.51(3H,s), 3.72–4.20(4H,m), 5.00(1H,s).

Analysis for C$_{32}$H$_{33}$F$_3$N$_4$O$_7$: Calcd. (%): C,59.81 H,5.18 N,8.72. Found (%): C,59.76 H,5.42 N,8.59.

EXAMPLE 55

1,4-Dihydro-2,6-dimethyl-4-(2,3-dichlorophenyl)-3-methoxycarbonylpyridine-5-carboxylic acid 6-(4-phenyl-3-pyrazolyloxy)hexyl ester Aspect: Colorless powder.
IR Spectrum (CHCl$_3$) cm$^{-1}$: 3500, 3460, 1693.
PMR Spectrum (CDCl$_3$) δ: 0.95–1.97(8H,m), 2.27(6H,s), 3.57(3H,s), 3.70–4.21(4H,m), 5.44(1H,s), 6.75–7.80(8H,m).
Analysis for C$_{31}$H$_{33}$Cl$_2$N$_3$O$_5$: Calcd. (%): C,62.21 H,5.56 N,7.02. Found (%): C,62.33 H,5.80 N,7.01.

EXAMPLE 56

1,4-Dihydro-2,6-dimethyl-4-(3-nitrophenyl)-3-ethoxycarbonylpyridine-5-carboxylic acid 6-(5-o-tolyl-3-pyrazolyloxy)hexyl ester Aspect: Pale yellow powder.
IR Spectrum (CHCl$_3$) cm$^{-1}$: 3500, 3463, 1692, 1520, 1345.
PMR Spectrum (DMSO-d$_6$) δ: 0.90–1.95(8H,m), 1.17(3H,t), 2.30(6H,s), 2.35(3H,s), 3.74–4.21(6H,m), 5.00(1H,s), 5.87(1H,s), 7.00–8.08(8H,m), 8.90(1H,s), 11.83(1H, broad).
Analysis for C$_{33}$H$_{38}$N$_4$O$_7$: Calcd. (%): C,65.77 H,6.36 N,9.30. Found (%): C,65.89 H,6.40 N,9.16.

EXAMPLE 57

1,4-Dihydro-2,6-dimethyl-4-(2-nitrophenyl)-3-ethoxycarbonylpyridine-5-carboxylic acid 6-(5-o-tolyl-3-pyrazolyloxy)hexyl ester Aspect: Pale yellow powder.
IR Spectrum (CHCl$_3$) cm$^{-1}$: 3500, 3462, 1693, 1520, 1345.
PMR Spectrum (DMSO-d$_6$) δ: 0.97–2.00(11H,m), 2.22(3H,s), 2.28(3H,s), 2.35(3H,s), 3.72–4.21(6H,m), 5.53(1H,s), 5.86(1H,s), 7.00–8.03(8H,m), 8.80(1H, broad).
Analysis for C$_{33}$H$_{38}$N$_4$O$_7$: Calcd. (%): C,65.77 H,6.36 N,9.30. Found (%): C,65.93 H,6.58 N,9.17.

EXAMPLE 58

1,4-Dihydro-2,6-dimethyl-4-(2-nitrophenyl)-3-ethoxycarbonylpyridine-5-carboxylic acid 6-(5-p-chlorophenyl-3-pyrazolyloxy)hexyl ester Aspect: Pale yellow powder.
IR Spectrum (CHCl$_3$) cm$^{-1}$: 3500, 3460, 1692, 1520, 1345.
PMR Spectrum (DMSO-d$_6$) δ: 0.90–2.00(11H,m), 2.23(3H,s), 2.29(3H,s), 3.72–4.21(6H,m), 5.53(1H,s), 6.05(1H,s), 7.03–8.05(8H,m), 8.90(1H,s).
Analysis for C$_{32}$H$_{35}$ClN$_4$O$_7$: Calcd. (%): C,61.68 H,5.66 N,8.99. Found (%): C,61.47 H,5.75 N,9.20.

EXAMPLE 59

1,4-Dihydro-2,6-dimethyl-4-(3-nitrophenyl)-3-ethoxycarbonylpyridine-5-carboxylic acid 6-(5-p-chlorophenyl-3-pyrazolyloxy)-5-ethylhexyl ester Aspect: Pale yellow powder.
IR Spectrum (CHCl$_3$) cm$^{-1}$: 3500, 3460, 1695, 1522, 1345.
PMR Spectrum (DMSO-d$_6$) δ:
2.29(6H,s), 3.73–4.22(6H,m), 4.99(1H,s), 6.07(1H,s), 7.05–8.06(8H,m), 8.85(1H,s), 12.24(1H,s).
Analysis for C$_{34}$H$_{39}$ClN$_4$O$_7$: Calcd. (%): C,62.71 H,6.04 N,8.60. Found (%): C,62.99 H,6.21 N,8.47.

EXAMPLE 60

1,4-Dihydro-2,6-dimethyl-4-(2,3-dichlorophenyl)-3-methoxycarbonylpyridine-5-carboxylic acid 6-(5-p-nitrophenyl-3-pyrazolyloxy)hexyl ester Aspect: Pale yellow powder.
IR Spectrum (CHCl$_3$) cm$^{-1}$: 3500, 3468, 1690.
PMR Spectrum (DMSO-d$_6$) δ: 0.95–2.00(8H,m), 2.25(6H,s), 3.48(3H,s), 3.70–4.20(4H,m), 5.32(1H,s), 6.26(1H,s), 6.87–8.30(8H,m), 8.76(1H, broad).
Analysis for C$_{31}$H$_{32}$Cl$_2$N$_4$O$_7$: Calcd. (%): C,57.86 H,5.01 N,8.71. Found (%): C,57.84 H,5.20 N,8.63.

EXAMPLE 61

1,4-Dihydro-2,6-dimethyl-4-(2-nitrophenyl)-3-methoxycarbonylpyridine-5-carboxylic acid 6-(5-p-methoxyphenyl-3-pyrazolyloxy)hexyl ester Aspect: Yellow powder.
IR Spectrum (CHCl$_3$) cm$^{-1}$: 3500, 3465, 1695, 1520, 1345.
PMR Spectrum (DMSO-d$_6$) δ: 0.96–2.00(8H,m), 2.23(3H,s), 2.29(3H,s), 3.44(3H,s), 3.73(3H,s), 3.73–4.20(4H,m), 5.53(1H,s), 5.98(1H,s), 6.73–8.10(8H,m), 8.80(1H,s).
Analysis for C$_{32}$H$_{36}$N$_4$O$_8$: Calcd. (%): C,63.56 H,6.00 N,9.27. Found (%): C,63.70 H,6.02 N,9.09.

EXAMPLE 62

1,4-Dihydro-2,6-dimethyl-4-(3-nitrophenyl)-3-methoxycarbonylpyridine-5-carboxylic acid 6-[5-(p-N-acetylaminophenyl)-3-pyrazolyloxy]hexyl ester Aspect: Pale yellow powder.
IR Spectrum (CHCl$_3$) cm$^{-1}$: 3500, 3460, 3420, 1695, 1520, 1345.
PMR Spectrum (CDCl$_3$+D$_2$O) δ: 0.95–2.00(8H,m), 2.13(3H,s), 2.30(6H,s), 3.55(3H,s), 3.74–4.22(4H,m), 5.07(1H,s), 5.91(1H,s), 7.00–8.07(8H,m).
Analysis for C$_{33}$H$_{37}$N$_5$O$_8$: Calcd. (%): C,62.75 H,5.90 N,11.09. Found (%): C,62.89 H,5.74 N,11.20.

EXAMPLE 63

1,4-Dihydro-2,6-dimethyl-4-(3-nitrophenyl)-3-methoxycarbonylpyridine-5-carboxylic acid 6-(5-m-tolyl-3-pyrazolyloxy)hexyl ester Aspect: Pale yellow powder.
IR Spectrum (CHCl$_3$) cm$^{-1}$: 3500, 3460, 1690, 1520, 1345.
PMR Spectrum (CDCl$_3$) δ: 0.90–1.92(8H,m), 2.30(6H,s), 2.35(3H,s), 3.57(3H,s), 3.70–4.21(4H,m), 5.05(1H,s), 5.88(1H,s), 6.90–8.07(8H,m).
Analysis for C$_{32}$H$_{36}$N$_4$O$_7$: Calcd. (%): C,65.29 H,6.16 N,9.52. Found (%): C,65.33 H,6.01 N,9.76.

EXAMPLE 64

1,4-Dihydro-2,6-dimethyl-4-(3-nitrophenyl)-3-methoxycarbonylpyridine-5-carboxylic acid 6-(5-p-tolyl-3-pyrazolyloxy)hexyl ester Aspect: Pale yellow powder.
IR Spectrum (CHCl$_3$) cm$^{-1}$: 3500, 3463, 1692, 1521, 1345.
PMR Spectrum (CDCl$_3$) δ: 0.96–1.95(8H,m), 2.30(6H,s), 2.34(3H,s), 3.56(3H,s), 3.74–4.20(4H,m), 5.04(1H,s), 5.88(1H,s), 6.89–8.05(8H,m).
Analysis for C$_{32}$H$_{36}$N$_4$O$_7$: Calcd. (%): C,65.29 H,6.16 N,9.52. Found (%): C,65.43 H,6.31 N,9.44.

EXAMPLE 65

1,4-Dihydro-2,6-dimethyl-4-(3-nitrophenyl)-3-ethoxycarbonylpyridine-5-carboxylic acid 6-(5-phenyl-3-pyrazolyloxy)hexyl ester Aspect: Pale yellow crystals.
Melting point: 156°–159° C. (from ethanol).
IR Spectrum (CHCl$_3$) cm$^{-1}$: 3500, 3460, 1693, 1520, 1345.
PMR Spectrum (CDCl$_3$+D$_2$O) δ: 0.90–1.90(8H,m), 1.17(3H,t), 2.32(6H,s), 3.72–4.22(6H,m), 5.04(1H,s), 5.87(1H,s), 6.92–8.06(8H,m).
Analysis for C$_{32}$H$_{36}$N$_4$O$_7$: Calcd. (%): C,65.29 H,6.16 N,9.52. Found (%): C,65.32 H,6.27 N,9.40.

EXAMPLE 66

1,4-Dihydro-2,6-dimethyl-4-(3-nitrophenyl)-3-methoxycarbonylpyridine-5-carboxylic acid 6-[5-(p-N,N-dimethylaminophenyl)-3-pyrazolyloxy]hexyl ester Aspect: Pale yellow powder.
IR Spectrum (CHCl$_3$) cm$^{-1}$: 3500, 3460, 1695, 1520, 1345.
PMR Spectrum (CDCl$_3$) δ: 0.90–1.90(8H,m), 2.30(6H,s), 2.90(6H,s), 3.55(3H,s), 3.71–4.20(4H,m), 5.07(1H,s).
Analysis for C$_{33}$H$_{39}$N$_5$O$_7$:
Calcd. (%): C,64.17 H,6.36 N,11.34. Found (%): C,64.10 H,6.54 N,11.20.

EXAMPLE 67

1,4-Dihydro-2,6-dimethyl-4-(3-nitrophenyl)-3-methoxycarbonylpyridine-5-carboxylic acid 6-[5-(m-N-ethylaminophenyl)-3-pyrazolyloxy]hexyl ester Aspect: Pale yellow powder.
IR Spectrum (CHCl$_3$) cm$^{-1}$: 3500, 3460, 1695, 1520, 1345.
PMR Spectrum (CDCl$_3$+D$_2$O) δ: 0.90–1.97(11H,m), 2.02(2H,q), 2.31(6H,s), 3.56(3H,s), 3.72–4.20(4H,m), 5.05(1H,s), 5.83(1H,s).
Analysis for C$_{33}$H$_{39}$N$_5$O$_7$: Calcd. (%): C,64.17 H,6.36 N,11.34. Found (%): C,64.03 H,6.47 N,11.46.

EXAMPLE 68

12.86 g (20 mmole) of 1,4-dihydro-2,6-dimethyl-4-(2,3-dichlorophenyl)-3-methoxycarbonylpyridine-5-carboxylic acid 6-(5-p-nitrophenyl-3-pyrazolyloxy)hexyl ester (Example 60) was dissolved in 100 ml of ethanol, to which was added 5 ml of Raney nickel, and catalytic hydrogenation was effected at room temperature and atmospheric pressure, thereby 1350 ml (60 mmole) of hydrogen was absorbed. The Raney nickel was filtered off from the reaction mixture, and the filtrate was concentrated under reduced pressure to obtain a pale yellow oily residue. This residue was purified by chromatography on a silica gel column using a mixed solution of chloroform-methanol (the ratio by volume of 3:1) as an eluent, and the fractions containing the intended compound were concentrated under reduced pressure to obtain a pale yellow oily residue. This residue was dissolved in ethyl acetate, and after adding 5 g of activated charcoal, stirred well, and filtered. The filtrate was concentrated to dryness under reduced pressure to obtain 6.63 g (yield 54.0%) of the 1,4-dihydro-2,6-dimethyl-4-(2,3-dichlorophenyl)-3-methoxycarbonylpyridine-5-carboxylic acid 6-(5-p-aminophenyl-3-pyrazolyloxy)hexyl ester as a pale yellow powder.
IR Spectrum (CHCl$_3$) cm$^{-1}$: 3500, 3460, 1695.
PMR Spectrum (CDCl$_3$+D$_2$O) δ: 0.95–1.95(8H,m), 2.26(6H,s), 3.58(3H,s), 3.74–4.21(4H,m), 5.43(1H,s), 5.86(1H,s).
Analysis for C$_{31}$H$_{34}$Cl$_2$N$_4$O$_5$: Calcd. (%): C,60.69 H,5.59 N,9.13. Found (%): C,60.55 H,5.76 N,9.01.

EXAMPLE 69

To a suspension of 0.262 g of sodium hydride (55% dispersion in mineral oil) in 10 ml of N,N-dimethylformamide, 1.33 g (7 mmole) of 3-p-methoxyphenyl-5-pyrazolone was added portionwise with stirring under ice cooling. To the above mixture was added dropwise a solution of 3.05 g (5 mmole) of 1,4-dihydro-2,6-dimethyl-4-(2,3-dichlorophenyl)-3-methoxycarbonylpyridine-5-carboxylic acid 6-tosyloxyhexyl ester in 7 ml of N,N-dimethylformamide at 0° to 10° C. with stirring and then the mixture was heated at 80° C. for 3 hours. The resulting reaction mixture was poured into ice water, and the precipitate was extracted with ethyl acetate. The organic layer was washed with brine, dried over anhydrous sodium sulfate, and then evaporated in vacuo to obtain an oily residue. The residue was purified by silica gel column chromatography using a mixed solution of chloroform-methanol (the ratio by volume of 100:1) as an eluent, and the fractions containing desired compound were collected and evaporated in vacuo to dryness to give white crystalline residue. The residue was recrystallized from a mixed solution of ethyl acetate-normal hexane to give 1.87 g (yield 59.0%) of the 1,4-dihydro-2,6-dimethyl-4-(2,3-dichlorophenyl)-3-methoxycarbonylpyridine-5-carboxylic acid 6-(5-p-methoxyphenyl-3-pyrazolyloxy)hexyl ester as colorless needles.
Melting point: 146°–148° C.
IR Spectrum (CHCl$_3$) cm$^{-1}$: 3500, 3475, 1695, 1615.
PMR Spectrum (DMSO-d$_6$) δ: 0.91–1.91(8H,m), 2.20(3H,s), 2.23(3H,s), 3.44(3H,s), 3.67–4.19(4H,m), 3.70(3H,s), 5.25(1H,s), 5.87(1H,s), 6.70–7.63(7H,m), 8.64(1H, broad).
Analysis for C$_{32}$H$_{35}$Cl$_2$N$_3$O$_6$: Calcd. (%): C,61.15 H,5.61 N,6.69. Found (%): C,61.30 H,5.65 N,6.62.

In addition to the above Examples, the following compounds were also produced similarly.

1,4-Dihydro-2,6-dimethyl-4-(3-nitrophenyl)-3-(2-ethoxyethoxycarbonyl)pyridine-5-carboxylic acid 6-(5-p-chlorophenyl-3-pyrazolyloxy)hexyl ester.

1,4-Dihydro-2,6-dimethyl-4-(2-bromophenyl)-3-methoxycarbonylpyridine-5-carboxylic acid 6-(5-phenyl-3-pyrazolyloxy)hexyl ester.

1,4-Dihydro-2,6-dimethyl-4-(3-nitrophenyl)-3-methoxycarbonylpyridine-5-carboxylic acid 6-(5-m-iodophenyl-3-pyrazolyloxy)hexyl ester.

1,4-Dihydro-2,6-dimethyl-4-(2,6-dichlorophenyl)-3-methoxycarbonylpyridine-5-carboxylic acid 6-(5-phenyl-3-pyrazolyloxy)hexyl ester.

1,4-Dihydro-2,6-dimethyl-4-(3,4-dichlorophenyl)-3-methoxycarbonylpyridine-5-carboxylic acid 6-(5-phenyl-3-pyrazolyloxy)hexyl ester.

1,4-Dihydro-2,6-dimethyl-4-(3-nitrophenyl)-3-methoxycarbonylpyridine-5-carboxylic acid 6-[5-(2,4-dimethylphenyl)-3-pyrazolyloxy]hexyl ester.

1,4-Dihydro-2,6-dimethyl-4-(3-nitrophenyl)-3-methoxycarbonylpyridine-5-carboxylic acid 6-[5-(p-N-benzoylaminophenyl)-3-pyrazolyloxy]hexyl ester.

1,4-Dihydro-2,6-dimethyl-4-(3-nitrophenyl)-3-methoxycarbonylpyridine-5-carboxylic acid 6-[5-(p-N,N-diethylaminophenyl)-3-pyrazolyloxy]hexyl ester.
1,4-Dihydro-2,6-dimethyl-4-(3-nitrophenyl)-3-methoxycarbonylpyridine-5-carboxylic acid 6-(5-p-ethoxyphenyl-3-pyrazolyloxy)phenyl ester.
1,4-Dihydro-2,6-dimethyl-4-(3-nitrophenyl)-3-methoxycarbonylpyridine-5-carboxylic acid 6-(5-p-methoxybenzyl-3-pyrazolyloxy)hexyl ester.
1,4-Dihydro-2,6-dimethyl-4-(3-nitrophenyl)-3-methoxycarbonylpyridine-5-carboxylic acid 6-[5-(2,6-dimethylphenyl)-3-pyrazolyloxy]hexyl ester.
1,4-Dihydro-2,6-dimethyl-4-(3-nitrophenyl)-3-methoxycarbonylpyridine-5-carboxylic acid 6-(5-α-phenethyl-3-pyrazolyloxy)hexyl ester.
1,4-Dihydro-2,6-dimethyl-4-(3-nitrophenyl)-3-methoxycarbonylpyridine-5-carboxylic acid 6-(5-β-phenethyl-3-pyrazolyloxy)hexyl ester.
1,4-Dihydro-2,6-dimethyl-4-(3-nitrophenyl)-3-methoxycarbonylpyridine-5-carboxylic acid 6-[4-(3,4-methylenedioxyphenyl)-3-pyrazolyloxy]hexyl ester.
1,4-Dihydro-2,6-dimethyl-4-(3-nitrophenyl)-3-methoxycarbonylpyridine-5-carboxylic acid 6-[4-(2,6-dimethoxyphenyl)-3-pyrazolyloxy]hexyl ester.
1,4-Dihydro-2,6-dimethyl-4-(3-nitrophenyl)-3-methoxycarbonylpyridine-5-carboxylic acid 6-[4-(2,6-dimethylphenyl)-3-pyrazolyloxy]hexyl ester.
1,4-Dihydro-2,6-dimethyl-4-(3-nitrophenyl)-3-methoxycarbonylpyridine-5-carboxylic acid 6-(4-p-methoxyphenyl-3-pyrazolyloxy)hexyl ester.
1,4-Dihydro-2,6-dimethyl-4-(3-nitrophenyl)-3-methoxycarbonylpyridine-5-carboxylic acid 6-(4-o-chlorophenyl-3-pyrazolyloxy)hexyl ester.
1,4-Dihydro-2,6-dimethyl-4-(3-nitrophenyl)-3-methoxycarbonylpyridine-5-carboxylic acid 6-[5-(3,4-methylenedioxybenzyl)-3-pyrazolyloxy]hexyl ester.

What is claimed is:

1. A 1,4-dihydropyridine derivative of the following general formula [I]:

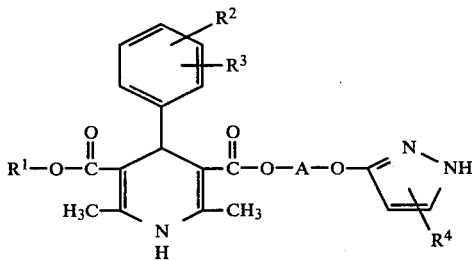

wherein $R^1$ represents an alkyl group having from 1 to 4 carbon atoms or an alkoxyalkyl group having from 3 to 6 carbon atoms, $R^2$ represents a hydrogen atom or a halogen atom, $R^3$ represents either a nitro group when $R^2$ is a hydrogen atom or a halogen atom when $R^2$ is a halogen atom, $R^4$ represents a pyridyl group, a phenethyl group, a benzyl group which may optionally be substituted by at least one member selected from the group consisting of a lower alkyl group, a lower alkoxy group, a methylenedioxy group and a halogen atom or a phenyl group which may optionally be substituted by at least one member selected from the group consisting of a lower alkyl group, a lower alkoxy group, a trifluoromethyl group, a nitro group, a cyano group, an amino group, a mono-lower-alkylamino group, a di-loweralkylamino group, an acetylamino group, a benzoylamino group, a methylenedioxy group and a halogen atom, and A represents a hexamethylene group which may optionally be substituted by one or two alkyl groups having from 1 to 3 carbon atoms.

2. A 1,4-dihydropyridine derivative according to claim 1, wherein $R^1$ represents one member selected from the group consisting of methyl, ethyl, propyl and butoxyethyl, $R^4$ represents one member selected from the group consisting of phenyl, fluorophenyl, chlorophenyl, tolyl, methoxyphenyl, dichlorophenyl, methylenedioxyphenyl, benzyl and pyridyl and A represents hexamethylene.

3. 1,4-Dihydro-2,6-dimethyl-4-(3-nitrophenyl)-3-methoxycarbonylpyridine-5-carboxylic acid 6-(5-phenyl-3-pyrazolyloxy)hexyl ester.

4. 1,4-Dihydro-2,6-dimethyl-4-(3-nitrophenyl)-3-methoxycarbonylpyridine-5-carboxylic acid 6-(5-m-fluorophenyl-3-pyrazolyloxy)hexyl ester.

5. 1,4-Dihydro-2,6-dimethyl-4-(2-nitrophenyl)-3-methoxycarbonylpyridine-5-carboxylic acid 6-(5-phenyl-3-pyrazolyloxy)hexyl ester.

6. 1,4-Dihydro-2,6-dimethyl-4-(3-nitrophenyl)-3-methoxycarbonylpyridine-5-carboxylic acid 6-(4-phenyl-3-pyrazolyloxy)hexyl ester.

7. 1,4-Dihydro-2,6-dimethyl-4-(3-nitrophenyl)-3-methoxycarbonylpyridine-5-carboxylic acid 6-(5-o-chlorophenyl-3-pyrazolyloxy)hexyl ester.

8. 1,4-Dihydro-2,6-dimethyl-4-(3-nitrophenyl)-3-normalpropoxycarbonylpyridine-5-carboxylic acid 6-[5-(2,4-dichlorophenyl)-3-pyrazolyloxy]hexyl ester.

9. 1,4-Dihydro-2,6-dimethyl-4-(3-nitrophenyl)-3-(2-isobutoxyethoxycarbonyl)pyridine-5-carboxylic acid 6-(5-m-fluorophenyl-3-pyrazolyloxy)hexyl ester.

10. 1,4-Dihydro-2,6-dimethyl-4-(3-nitrophenyl)-3-methoxycarbonylpyridine-5-carboxylic acid 6-(5-o-tolyl-3-pyrazolyloxy)hexyl ester.

11. 1,4-Dihydro-2,6-dimethyl-4-(3-nitrophenyl)-3-methoxycarbonylpyridine-5-carboxylic acid 6-[5-(2-pyridyl)-3-pyrazolyloxy]hexyl ester.

12. 1,4-Dihydro-2,6-dimethyl-4-(3-nitrophenyl)-3-methoxycarbonylpyridine-5-carboxylic acid 6-(5-benzyl-3-pyrazolyloxy)hexyl ester.

13. 1,4-Dihydro-2,6-dimethyl-4-(3-nitrophenyl)-3-methoxycarbonylpyridine-5-carboxylic acid 6-(5-p-methoxyphenyl-3-pyrazolyloxy)hexyl ester.

14. 1,4-Dihydro-2,6-dimethyl-4-(3-nitrophenyl)-3-methoxycarbonylpyridine-5-carboxylic acid 6-[5-(3,4-methylenedioxyphenyl)-3-pyrazolyloxy]hexyl ester.

15. 1,4-Dihydro-2,6-dimethyl-4-(2,3-dichlorophenyl)-3-methoxycarbonylpyridine-5-carboxylic acid 6-(5-phenyl-3-pyrazolyloxy)hexyl ester.

16. 1,4-Dihydro-2,6-dimethyl-4-(3-nitrophenyl)-3-ethoxycarbonylpyridine-5-carboxylic acid 6-(5-o-chlorophenyl-3-pyrazolyloxy)hexyl ester.

17. 1,4-Dihydro-2,6-dimethyl-4-(2,3-dichlorophenyl)-3-methoxycarbonylpyridine-5-carboxylic acid 6-(5-p-methoxyphenyl-3-pyrazolyloxy)hexyl ester.

18. 1,4-Dihydro-2,6-dimethyl-4-(3-nitrophenyl)-3-methoxycarbonylpyridine-5-carboxylic acid 6-(5-p-chlorophenyl-3-pyrazolyloxy)hexyl ester.

* * * * *